United States Patent
Meah

(10) Patent No.: US 11,701,281 B2
(45) Date of Patent: Jul. 18, 2023

(54) SURGICAL POSITIONING SYSTEM

(71) Applicant: Maaz Meah, Glen Ellyn, IL (US)

(72) Inventor: Maaz Meah, Glen Ellyn, IL (US)

( * ) Notice: Subject to any disclaimer, the term of this patent is extended or adjusted under 35 U.S.C. 154(b) by 292 days.

(21) Appl. No.: 16/059,757

(22) Filed: Aug. 9, 2018

(65) Prior Publication Data
US 2019/0046380 A1 Feb. 14, 2019

Related U.S. Application Data

(60) Provisional application No. 62/543,606, filed on Aug. 10, 2017.

(51) Int. Cl.
| | | |
|---|---|---|
| *A61G 13/02* | (2006.01) | |
| *A61G 13/12* | (2006.01) | |
| *A61G 13/10* | (2006.01) | |
| *A61G 7/065* | (2006.01) | |
| *A61B 17/00* | (2006.01) | |

(52) U.S. Cl.
CPC ............ *A61G 13/02* (2013.01); *A61G 13/10* (2013.01); *A61G 13/122* (2013.01); *A61G 13/123* (2013.01); *A61G 13/126* (2013.01); *A61G 13/1235* (2013.01); *A61G 13/1285* (2013.01); *A61B 17/00234* (2013.01); *A61G 7/065* (2013.01)

(58) Field of Classification Search
CPC .... A61G 13/02; A61G 13/122; A61G 13/126; A61G 13/12; A61G 13/1235; A61G 13/105; A61G 13/04; A61G 13/121; A61G 13/1225; A61G 13/123; A61G 13/124; A61G 13/1255; A61G 13/066; A61G 7/05; A61G 7/065; A61G 7/075; A61G 7/0755; A61G 13/00; A61G 13/06–10; A61G 13/1205; A61G 13/1245; A61G 13/128–1295; A61F 5/37; A61F 5/3776; A61F 5/3769; A41D 13/0518; A61B 5/704; A61B 6/0421; A61B 46/20; A61B 17/00234
USPC ...... 600/415; 5/621, 622, 624; 128/870, 845
See application file for complete search history.

(56) References Cited

U.S. PATENT DOCUMENTS

| | | | | |
|---|---|---|---|---|
| 4,601,075 A | * | 7/1986 | Smith | A61G 1/044 128/870 |
| 5,014,374 A | * | 5/1991 | Williams | A61G 1/04 5/628 |
| 6,653,363 B1 | | 11/2003 | Tursi, Jr. et al. | |

(Continued)

*Primary Examiner* — Michelle J Lee
*Assistant Examiner* — Robin Han
(74) *Attorney, Agent, or Firm* — Rocklaw PLLC; Michael T. Fluhler

(57) ABSTRACT

A positioning system for securing a patient relative to a surgical table is provided. The system may include a pad body, a plurality of pad straps and a plurality of body straps. The pad body may include an upper body portion, a lower body portion with first and second lower body extensions, and first and second arm extensions corresponding to the respective first and second lower body extensions. The plurality of pad straps may be configured to be positioned through at least one of the upper body and lower body portions. The plurality of body straps and the plurality of pad straps may be configured to engage each other. The system may include a support strip to increase friction and resist movement relative to the surgical table. A method of a positioning system is also provided.

19 Claims, 27 Drawing Sheets

(56) References Cited

U.S. PATENT DOCUMENTS

| | | |
|---|---|---|
| 8,464,720 B1 | 6/2013 | Pigazzi et al. |
| 8,511,314 B2 | 8/2013 | Pigazzi et al. |
| 8,569,911 B2 | 10/2013 | Burchard et al. |
| 8,661,580 B2 * | 3/2014 | Giap .................... A61G 7/1092 5/628 |
| 9,161,876 B2 | 10/2015 | Pigazzi et al. |
| 10,709,626 B1 * | 7/2020 | Gomez ................ A61G 13/127 |
| 2004/0123388 A1 | 7/2004 | Coppens et al. |
| 2008/0119722 A1 | 5/2008 | Swaney |
| 2008/0178389 A1 | 7/2008 | Bender |
| 2010/0275377 A1 | 11/2010 | West |
| 2011/0126355 A1 * | 6/2011 | Hiebert .............. A61G 13/1255 5/621 |
| 2012/0255124 A1 | 10/2012 | West |
| 2014/0366271 A1 * | 12/2014 | Marshall ............ A61G 13/1235 5/652 |
| 2016/0279007 A1 * | 9/2016 | Flatt ...................... A61F 5/3769 |
| 2017/0151116 A1 * | 6/2017 | Baker ................ A61G 13/1295 |

* cited by examiner

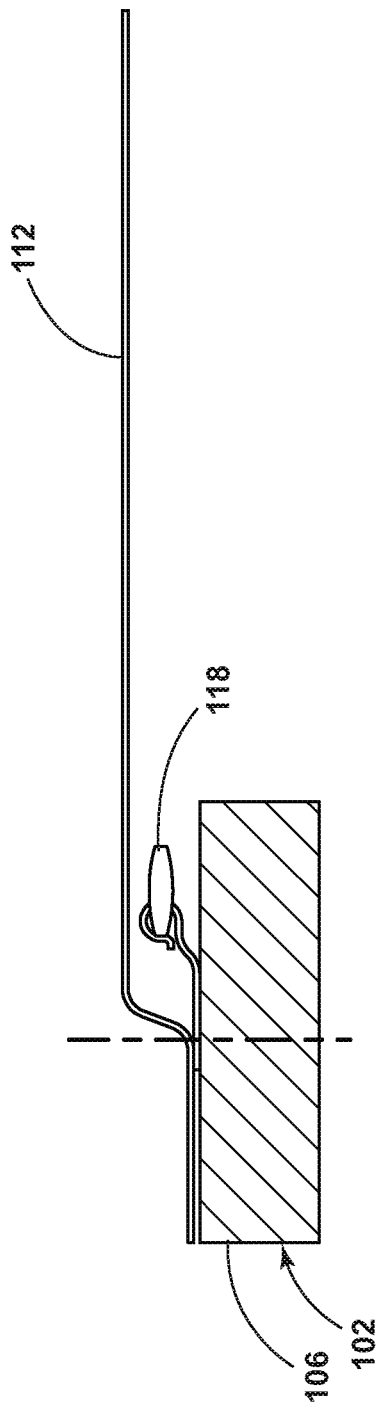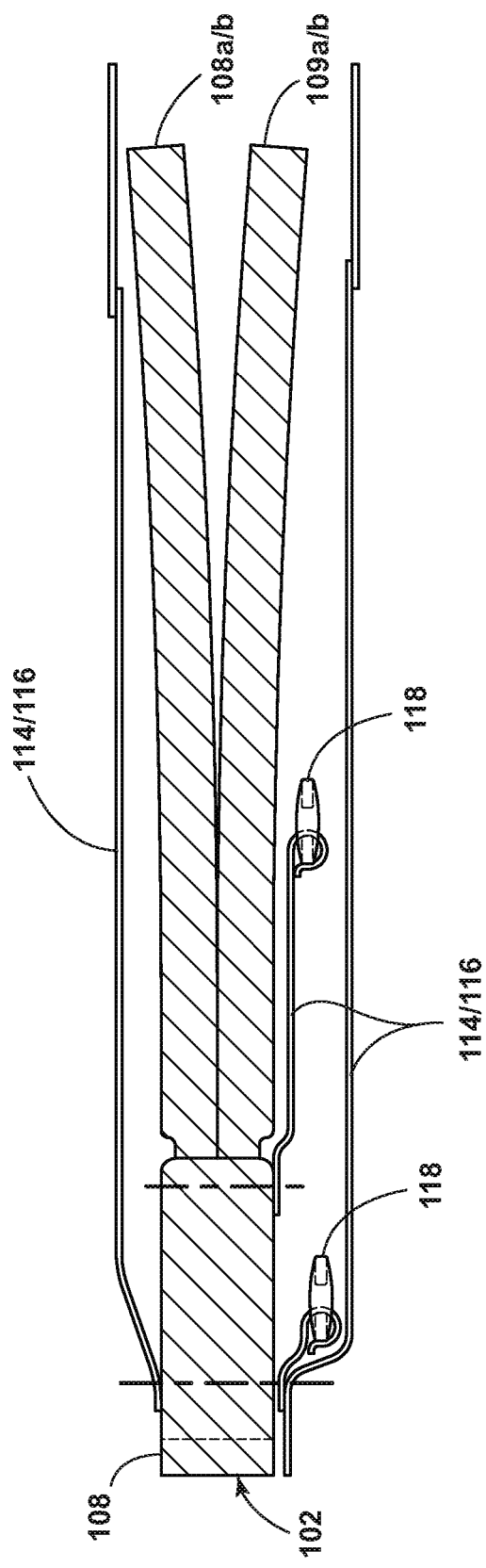

SURGICAL POSITIONING SYSTEM

CROSS-REFERENCE TO RELATED APPLICATIONS

This Non-Provisional Applications is based on and claims priority to U.S. Provisional Patent Application No. 62/543,606, filed on Aug. 10, 2017, which is hereby incorporated by reference in its entirety.

BRIEF DESCRIPTION OF THE DRAWINGS

While the claims are not limited to a specific illustration, an appreciation of the various aspects is best gained through a discussion of various examples thereof. Referring now to the drawings, exemplary illustrations are shown in detail. Although the drawings represent the illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrations are described in detail by referring to the drawings as follows:

FIG. 32 illustrates a top view of an exemplary strap and buckle assembly of FIGS. 25-26;

FIG. 33 illustrates a top view of another exemplary strap and buckle assembly of FIGS. 25-26.

DETAILED DESCRIPTION

A positioning system may be configured for positioning a patient on a surgical table during a surgical or medical procedure. The positioning system may be configured for robotic, laparoscopic, open or minimally invasive surgery. The positioning system may be configured to secure the patient to the table while in a Trendelenburg, reverse Trendelenburg or lateral tilt position. The positioning system may include a pad body, an anti-skid strip, a plurality of pad and body straps to secure the pad body and patient relative to the table. The pad body may include or be attached to waist and arm supports configured to engage the waist, one arm, or both arms of the patient or any combination thereof. The positioning system may include a foam, latex-free, high density, high viscosity, capillary action, or water wicking material or any combination thereof.

The pad body may include an upper extension, an upper body or chest portion, a lower body or waist portion, and a bottom recess. The pad body may include a plurality of slots or holes for receiving a first pad strap through the upper body or chest portion, a second pad strap through the lower body or waist portion, a third pad strap through the lower body or waist portion, and one or a plurality of body or chest straps configured to engage and connect respective first and second ends of the first, second, and third pad straps. The system may include a first buckle on a first portion of the second pad strap, a second buckle on a second portion of the second pad strap, a third buckle on a first portion of the third pad strap, and a fourth buckle on a second portion of the third pad strap. The system may include a support strip attached to the pad body, e.g., by way of stitching and/or an adhesive. The support strip may include an anti-slip tape or a textured surface with perforations, ribs, dimples, bumps, or a lattice structure. The support strip may be positioned transverse to the first, second, and third pad straps. Any of the pad or body straps may include a fastening side with a hook and loop fastener.

Methods of providing and using a positioning system are also contemplated. A method may include providing a pad body including an upper extension, an upper body or chest portion, a lower body or waist portion, and a bottom recess. The method may further including positioning a first pad strap through and relative to the upper body or chest portion, a second pad strap through and relative to the lower body or waist portion, and a third pad strap through and relative to the lower body or waist portion. The method may further include positioning one or a plurality of body or chest straps so as to connect respective first and second ends of the first, second, and third pad straps.

Figure 1:
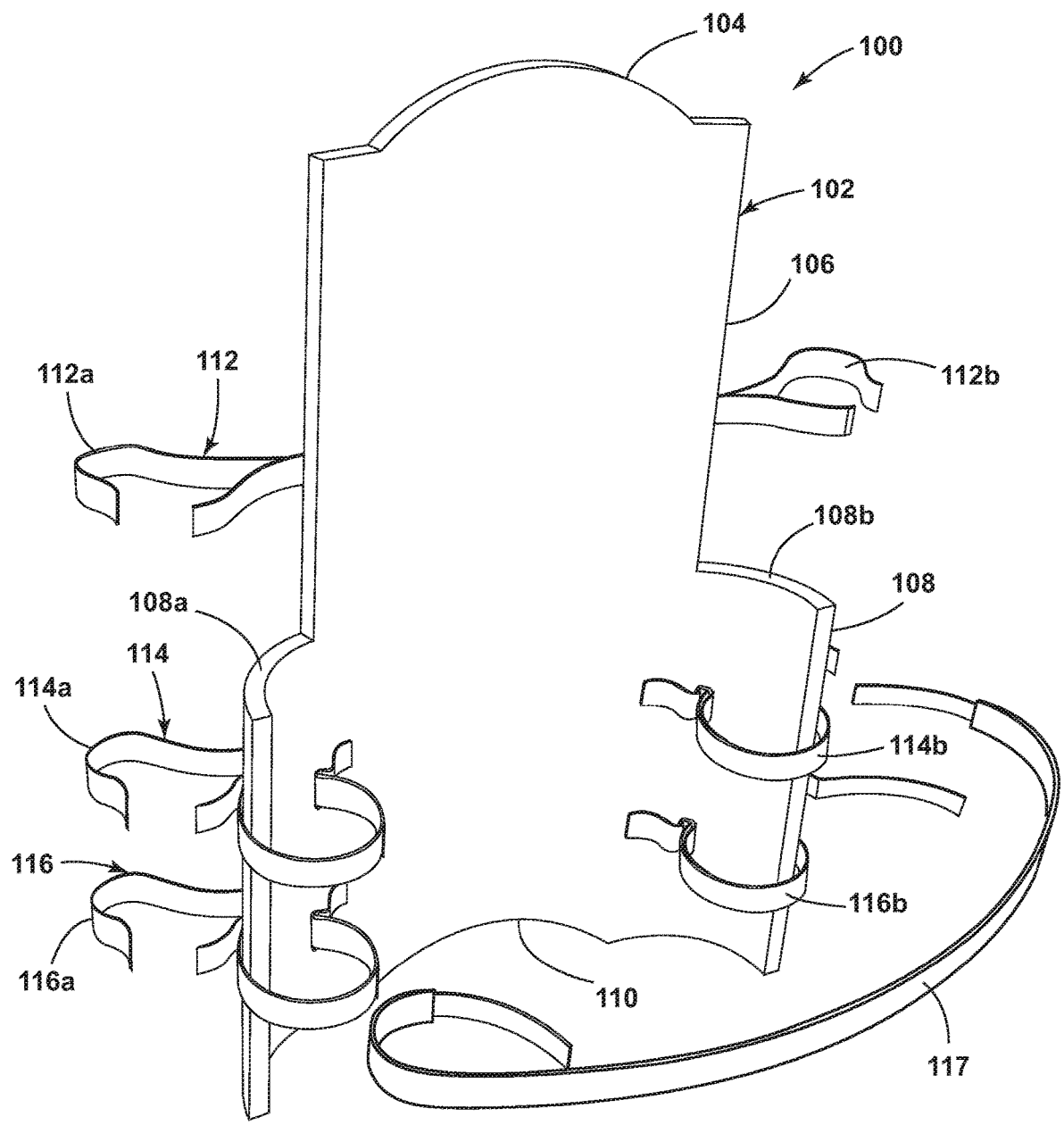
FIG. 1 illustrates an perspective view of an exemplary positioning system of the present disclosure.
Figure 2:
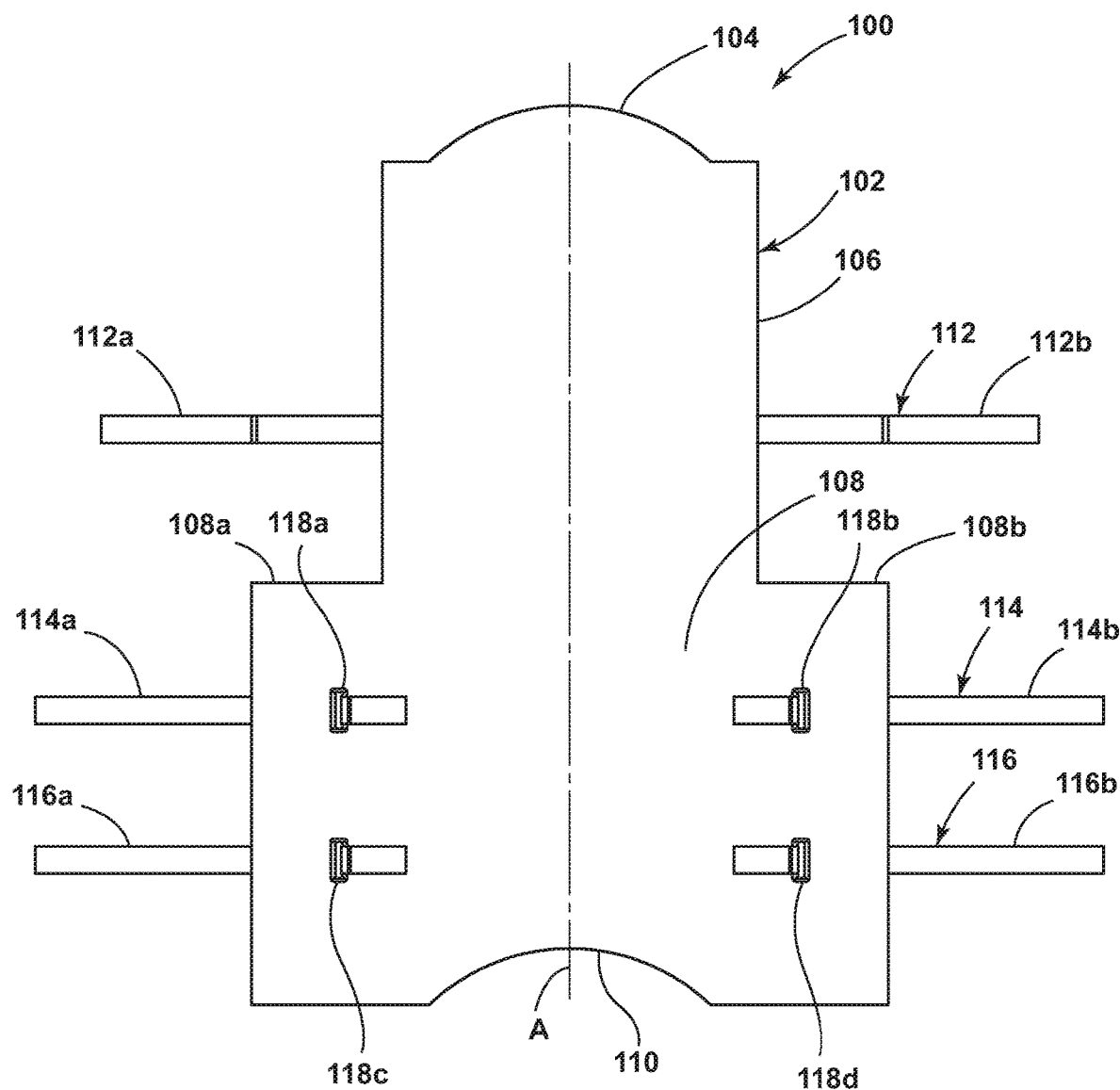
FIG. 2 illustrates a front view of the exemplary positioning system of FIG. 1.
Figure 3:
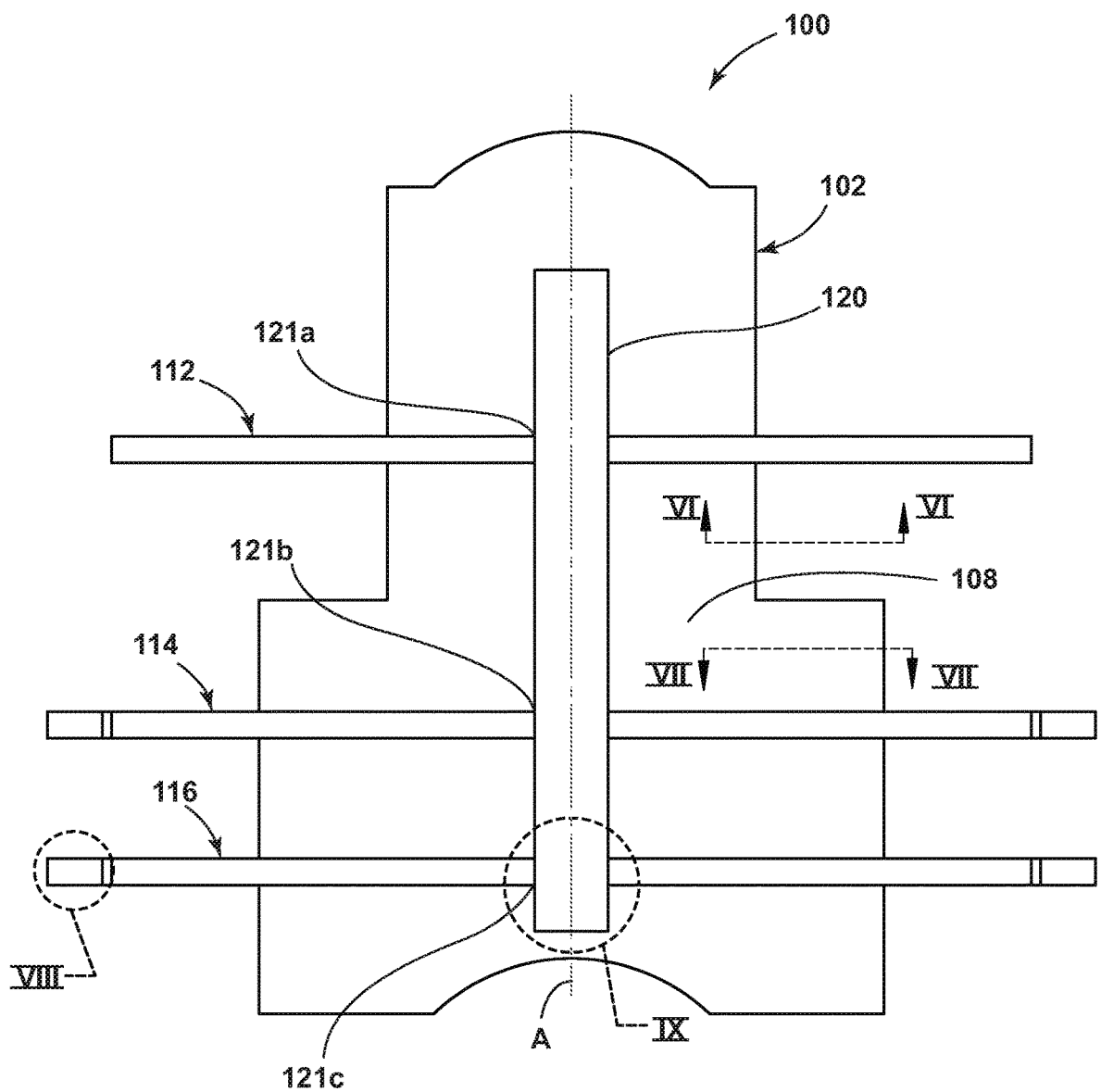
FIG. 3 illustrates a rear view of the exemplary positioning system of FIG. 1.

FIGS. 1-3 illustrate an exemplary positioning system 100. System 100 may include a pad body 102. Pad body 102 may be made of a flexible material such as foam, e.g., medical grade foam. As shown in FIG. 1, the pad body 102 may include an upper extension 104, an upper body or chest portion 106, a lower body or waist portion 108, and a bottom recess 110. The pad body 102 may include one or a plurality of slots or holes for receiving a plurality of pad straps, e.g., a first pad strap 112 along and/or through the upper body or chest portion, a second pad strap 114 along and/or through the lower body or waist portion 108, and a third pad strap 116 along and/or through the lower body or waist portion 108. One or a plurality of body or chest straps 117 configured to engage the respective first, second, and third pad straps 112, 114, 116. The ends of the first, second, and third pad straps 112, 114, 116 may be configured as a hook to engage the respective one or a plurality of body or chest straps 117. Straps 112, 114, 116, 117 may include a hook and loop fastener strip (e.g., Velcro).

Referring to FIG. 2, the lower body or waist portion 108 may include first and second lower body extensions 108A, 108B. Lower body portion 108 may include or be attached to lower body extensions 108A, 108B. Lower body extensions 108A, 108B may extend transversely from a central, longitudinal axis A of system 100. Lower body extensions 108A, 108B may be configured to engage a body, e.g., waist, torso, one or both arms of a patient or a combination thereof.

The system 100 may include a first buckle 118a on a first portion 114a of the second pad strap 114, a second buckle 118b on a second portion 114b of the second pad strap 114, a third buckle 118c on a first portion 116b of the third pad strap 116, and a fourth buckle 118d on a second portion 116b of the third pad strap 116. The one or a plurality of body or chest straps 117 may be configured to engage and connect respective first and second portions of the first, second, and third pad straps 112, 114, 116.

As shown in FIG. 3, the system 100 may include support strip 120 attached to the pad body 102. The support strip 120 may include a tape, e.g., anti-slip tape. The support strip 120 may be positioned transverse to the first, second, and third pad straps 112, 114, 116 and between the pad body 102 and any or all of straps 112, 114, 116. Support strip 120 may include a textured surface having a plurality of perforations, ribs, dimples, bumps, or a lattice structure. Support strip 120 may be configured to increase friction and reduce slip relative to a surgical table. Support strip 120, alone or in combination with any of the straps and/or support strip herein, may be configured to support a substantial portion or majority of the weight of a patient to increase friction and prevent or minimize slippage relative to the surgical table while in Trendelenburg, reverse Trendelenburg or lateral tilt position.

Figure 4:
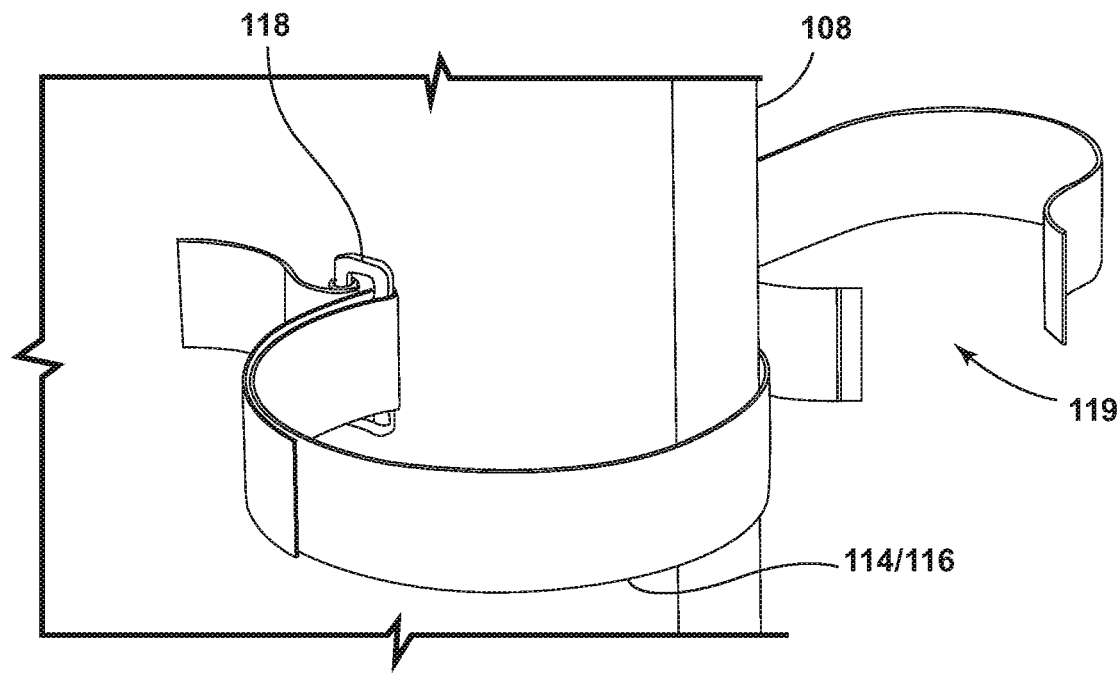
FIG. 4 illustrates a closer view of the exemplary positioning system including, for example, a strap and buckle assembly.

FIG. 4 illustrates system 100 including, for example, a strap and a buckle assembly including strap 114/116. System 100 may include strap 114/116 positioned through and about the pad body 102, e.g., lower body or waist portion 108. Straps 114, 116 may further include a hook portion 119 configured to engage the respective one or a plurality of body or chest straps 117.

Figure 5:
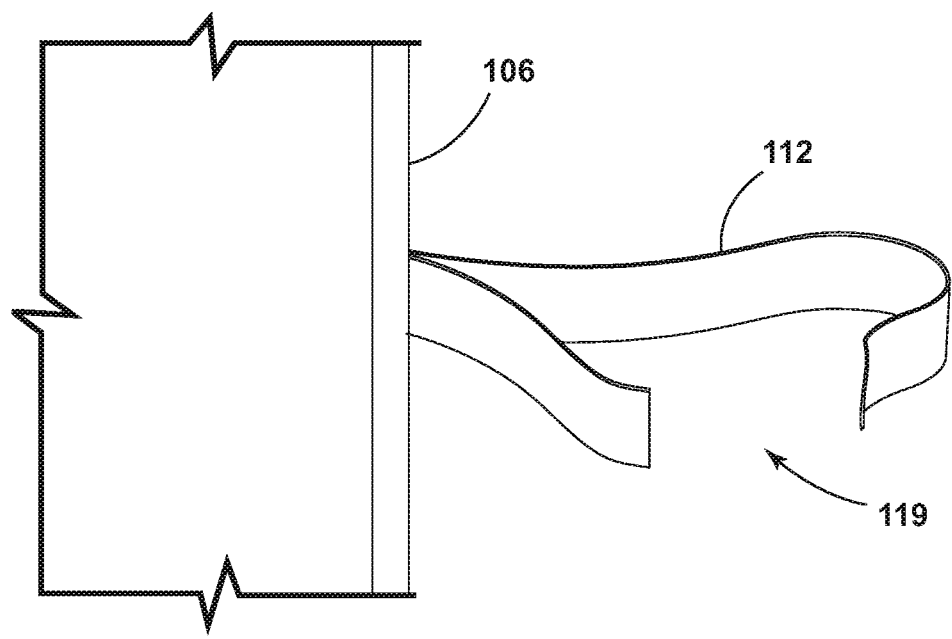
FIG. 5 illustrates a closer view of the exemplary positioning system including, for example, a strap assembly.

FIG. 5 illustrates system 100 including, for example, a strap assembly of strap 112. Strap 112 may be secured to the pad body 102, e.g., upper body or chest portion 106. Strap 112 may include hook portion 119 configured to engage the respective one or a plurality of body or chest straps 117.

Figure 6:
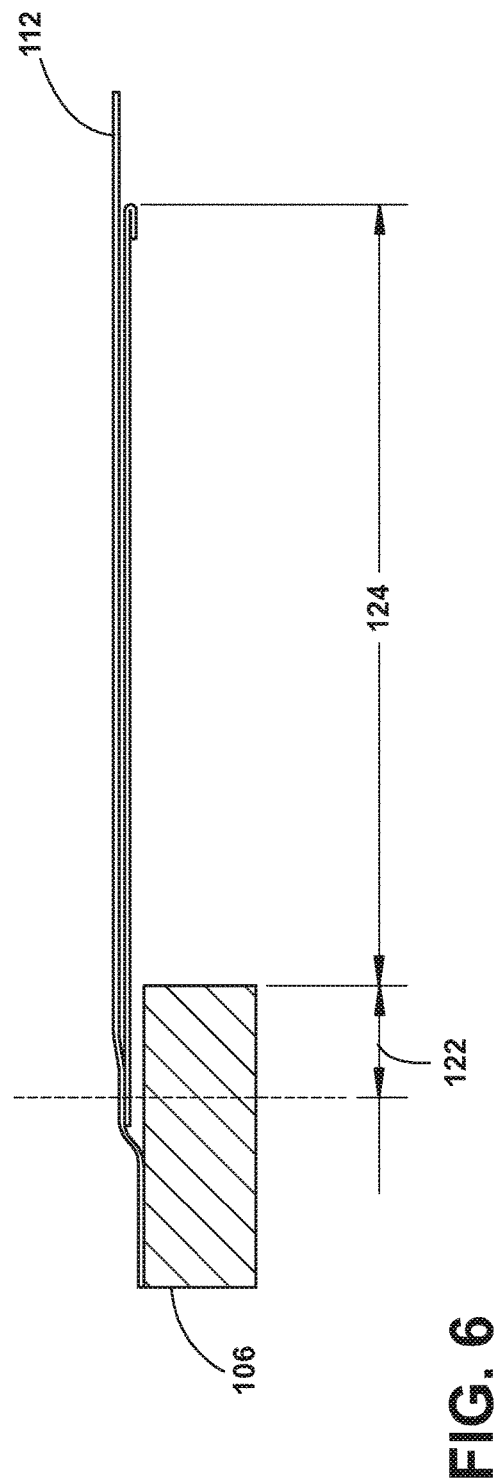
FIG. 6 illustrates a top view of an exemplary strap assembly of FIG. 5.

FIG. 6 illustrates strap 112 secured to and/or through the upper body or chest portion 106. Strap 112 include first and second layers on a front side of upper body or chest portion 106. The first layer may be secured to the upper body or chest portion 106 and positioned along the second layer. The second layer may include a first end secured to an inner side of the first layer and a second end that is folded and hemmed. Strap 112 may include a predefined dimension 122 (e.g., about 1 inch) and a predefined dimension 124 (e.g., about 7 inches). Alternatively or in addition, strap 112 may be secured on or through an upper portion of lower body portion 108, and/or a lower portion of lower body portion 108

Figure 7:
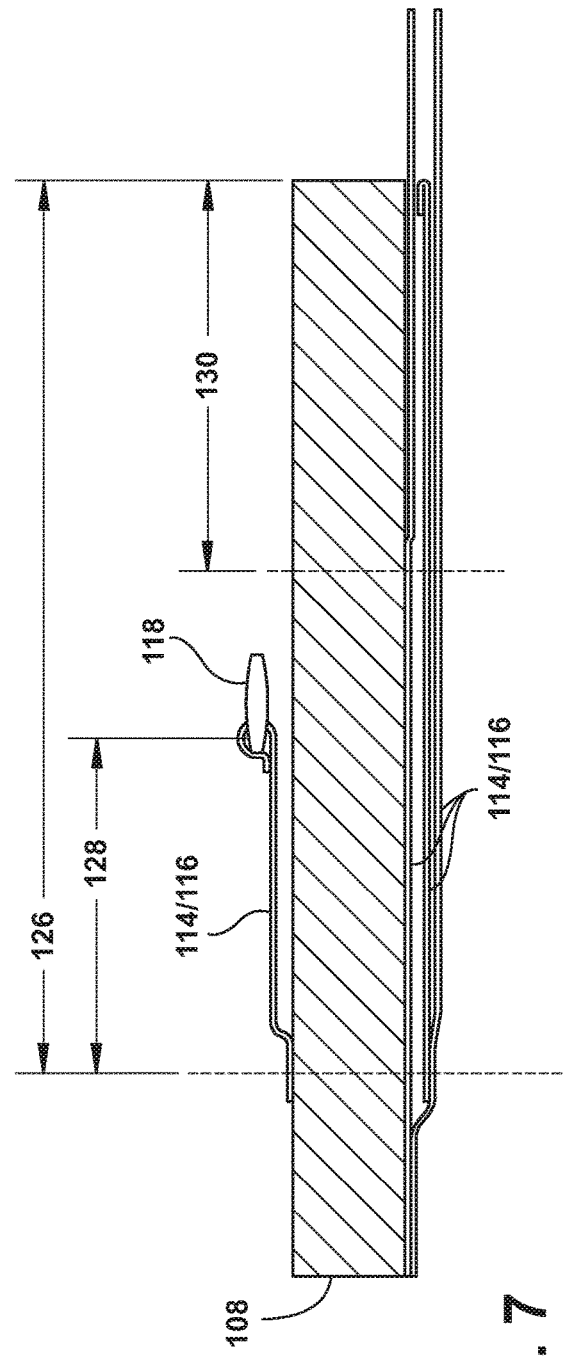
FIG. 7 illustrates a top view of an exemplary strap and buckle assembly of FIG. 4.

FIG. 7 illustrates strap 114/116 secured to and/or through lower body or waist portion 108. Strap 114/116 may include a first layer on a front side of lower body or waist portion 108 and second, third and fourth layers on a back side of lower body or waist portion 108. The first layer may include a first end secured to a front side of the lower body or waist portion 108. The second layer may be secured along the back side of lower body or waist portion 108. The third layer may be positioned between the second layer and the third layer. The fourth layer may include a first end secured to the second layer, a middle portion secured to the third layer, and may extend along the third layer. Strap 114/116 may include a predefined dimension 126 (e.g., about 8 inches), a predefined dimension 128 (e.g., about 3 inches), and a predefined dimension 130 (e.g., about 3.5 inches). Alternatively or addition, strap 114/116 may be secured to and/or through upper body or waist portion 106.

Figure 8:
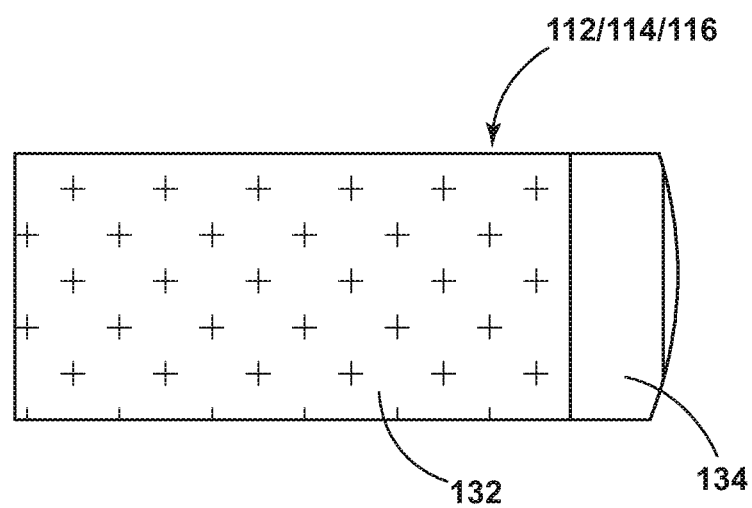
FIG. 8 illustrates a closer view of an exemplary strap assembly of the present disclosure.
Figure 9:
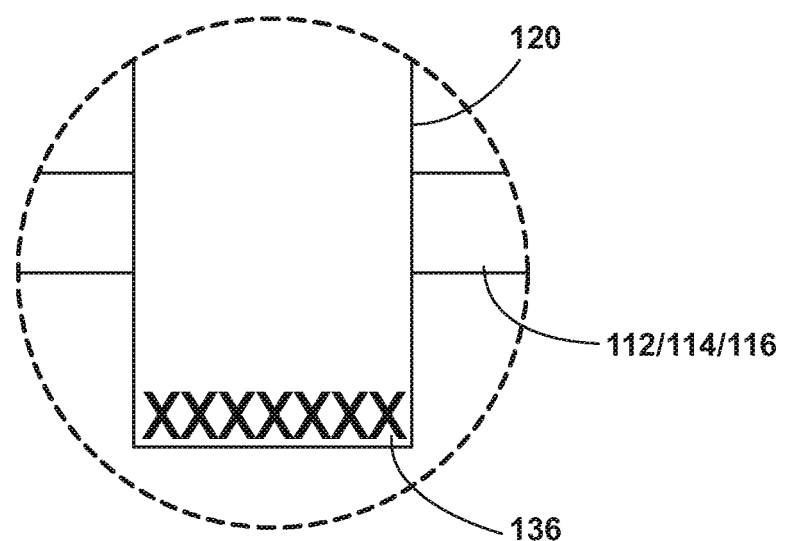
FIG. 9 illustrates a closer, rear view of the exemplary positioning system.
Figure 10:
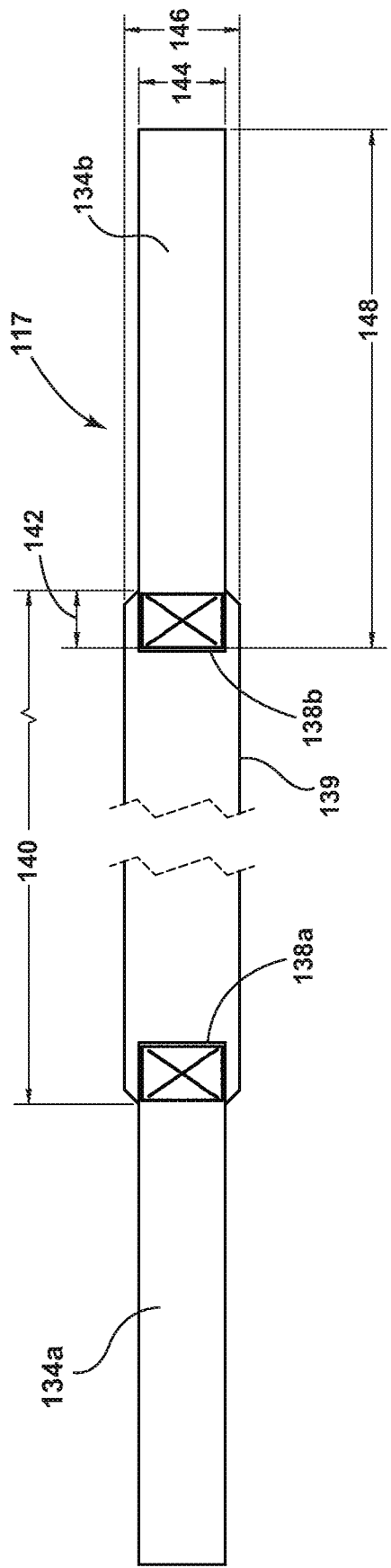
FIG. 10 illustrates a view of a strap assembly of the present disclosure.
Figure 11:
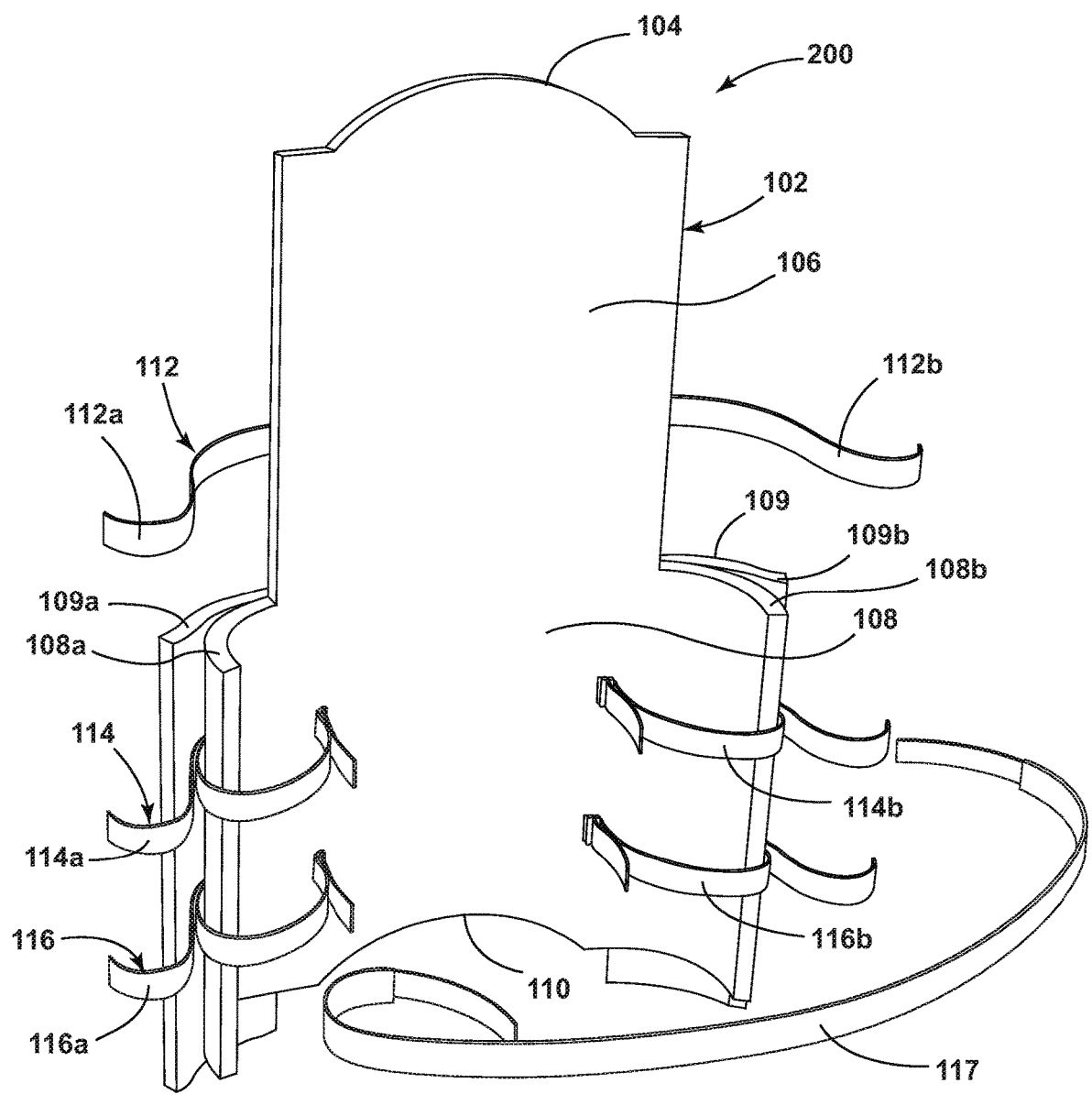
FIG. 11 illustrates an perspective view of another exemplary positioning system of the present disclosure.

FIGS. 8-10 illustrate closer views of the straps herein. As shown in FIG. 8, strap 112/114/116 may include stitch pattern 132 securing strap 112/114/116 to hook and loop fastener 134. With reference to FIG. 9, strap 112/114/116 may be positioned under tape 120 and with tape 120 having stitch pattern 136 on one or both sides thereof.

Referring to FIG. 10, strap 117 may include first and second strap portions 134a, 134b (e.g., with a fastener layer), stitch patterns 138a, 138b, and middle portion 139. Strap 117 may include a predefined dimension 140 (e.g., about 60 inches), a predefined dimension 142 (e.g., about 1 inch), a predefined dimension 144 (e.g., about 1.5 inches), a predefined dimension 146 (e.g., about 2 inches), and a predefined dimension 148 (e.g., about 9 inches).

FIGS. 11-24 illustrate system 200 that may include all or any portions of system 100 as described above with respect to FIGS. 1-10. As shown in FIGS. 11-24, system 200 may include similar or different structures and components than system 100. System 200 may include a pad body 102. Pad body 102 may be made of a flexible material such as foam, e.g., medical grade foam.

Figure 12:
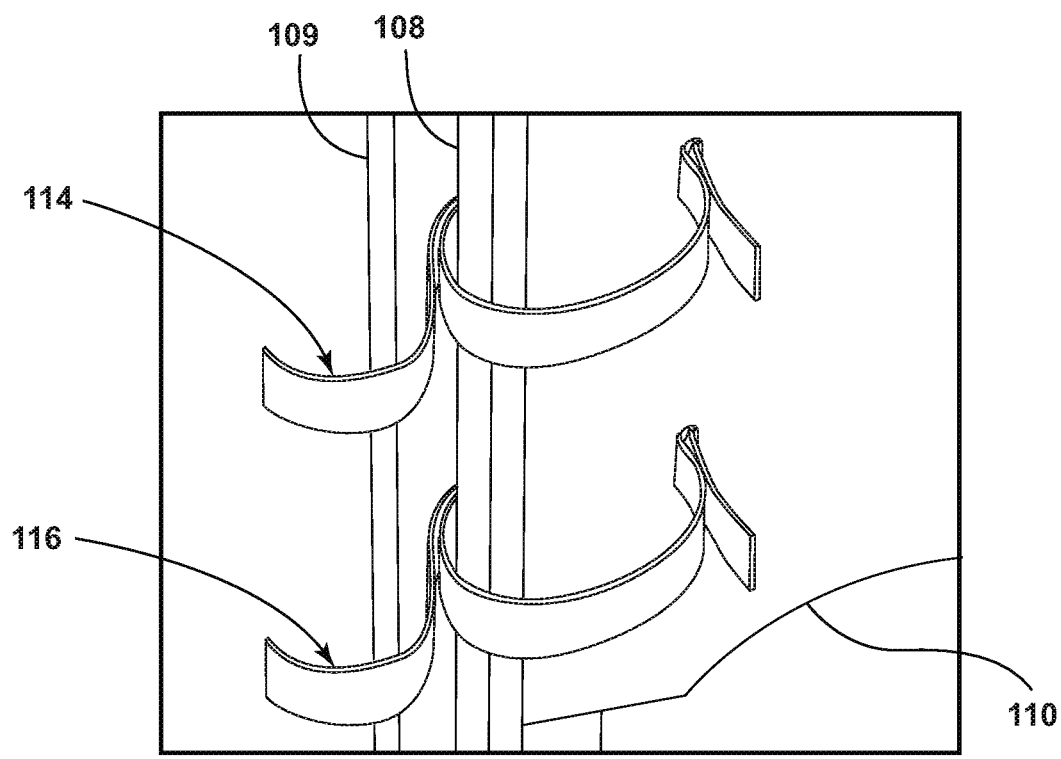
FIG. 12 illustrates a perspective view of the exemplary positioning system of FIG. 11.
Figure 13:
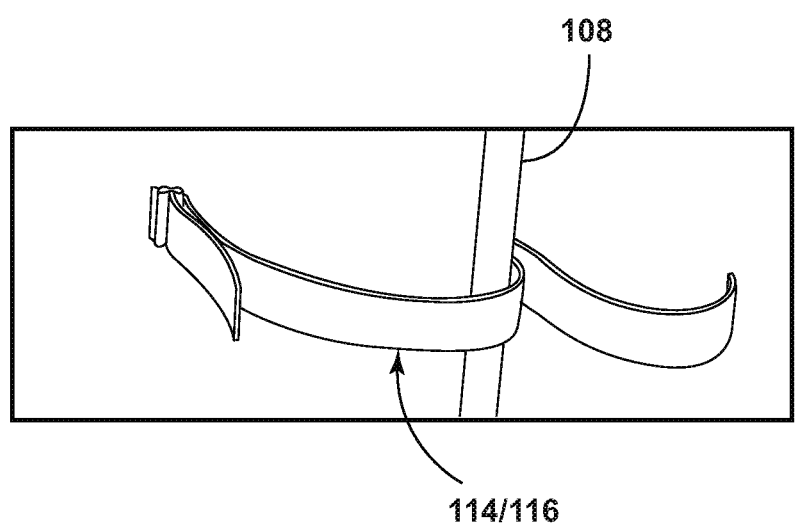
FIG. 13 illustrates a perspective view of the exemplary positioning system of FIG. 11.
Figure 14:
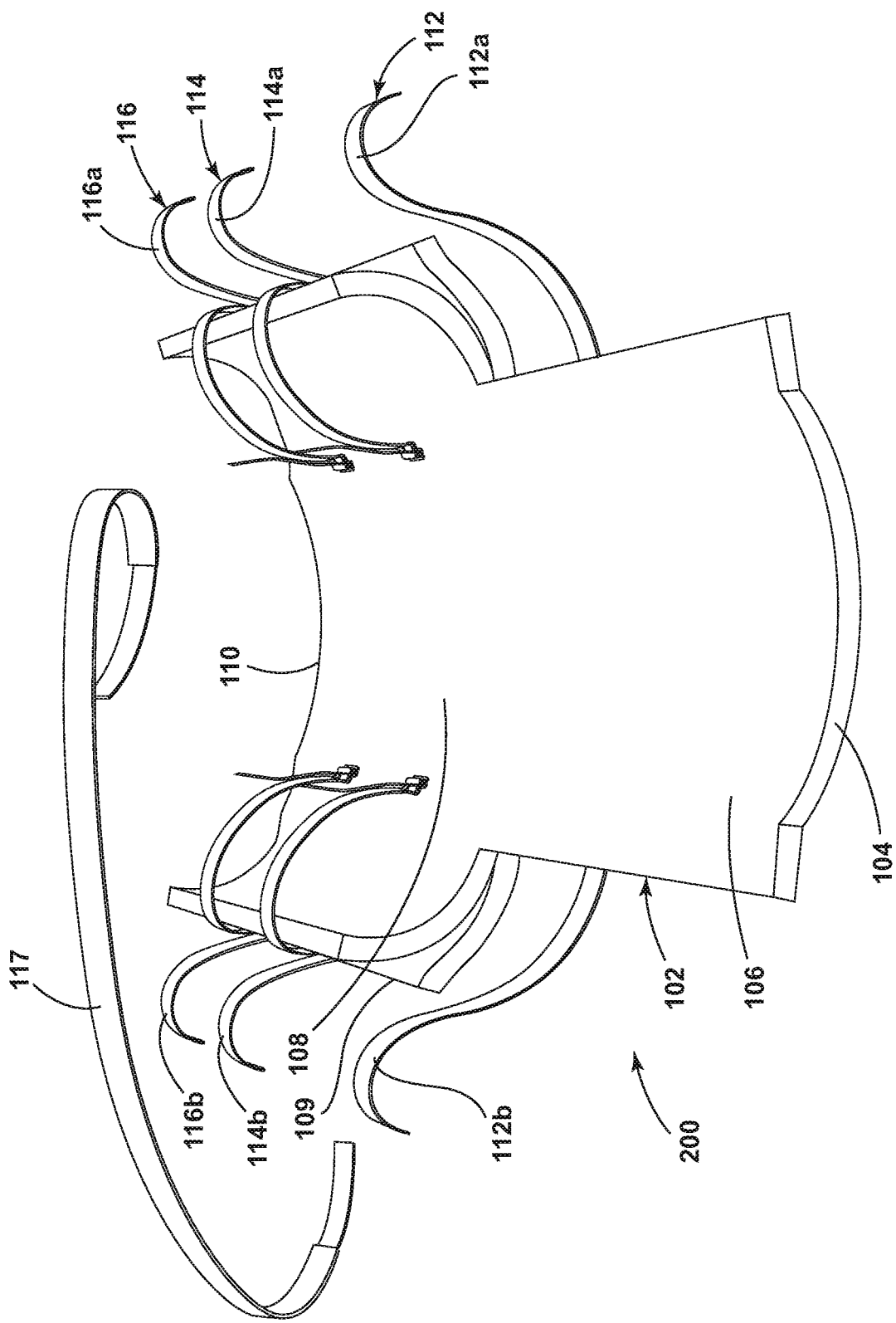
FIG. 14 illustrates a top, perspective view of the exemplary positioning system of FIG. 11.
Figure 15:
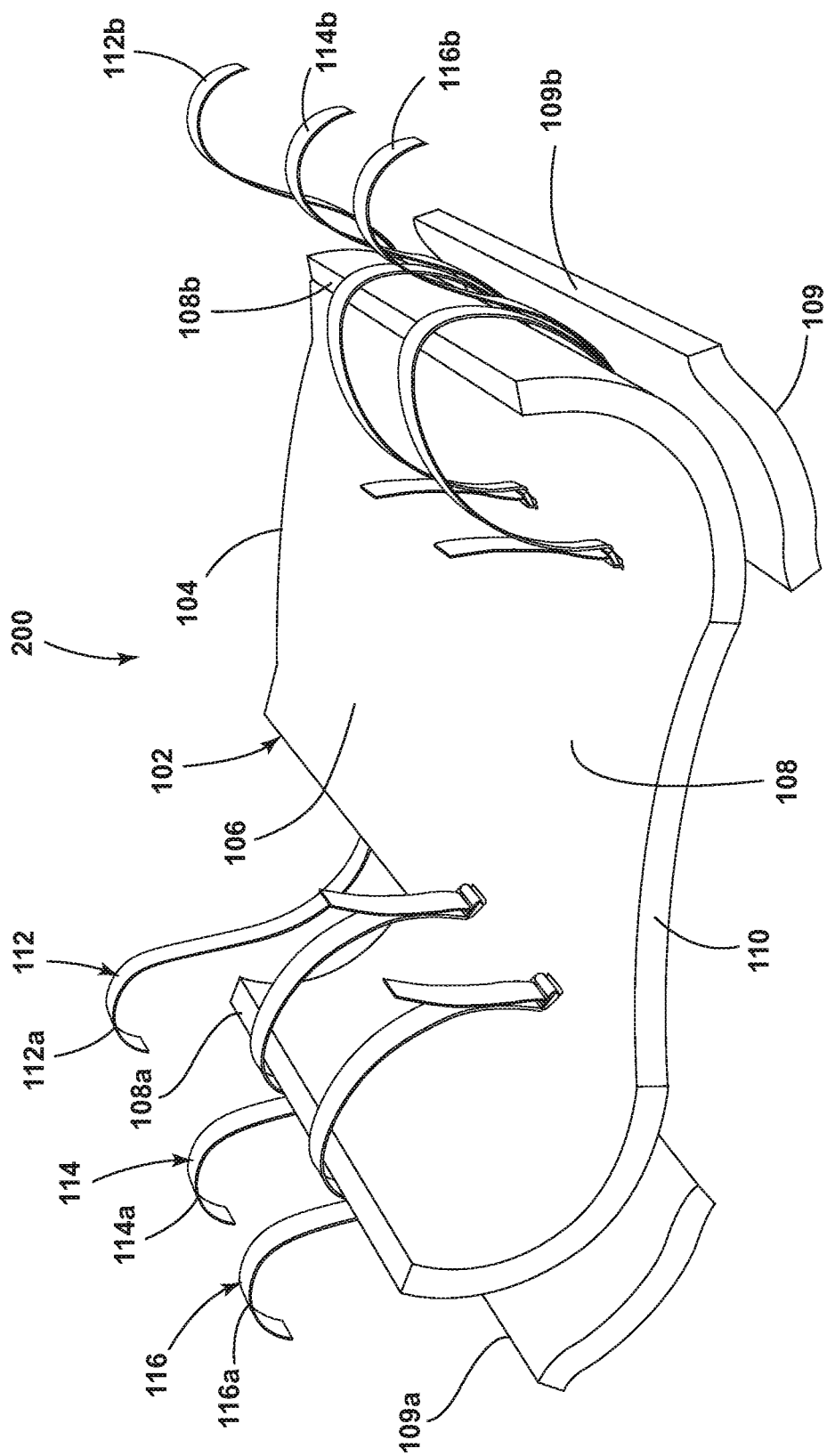
FIG. 15 illustrates a bottom, perspective view of the exemplary positioning system of FIG. 11.
Figure 16:
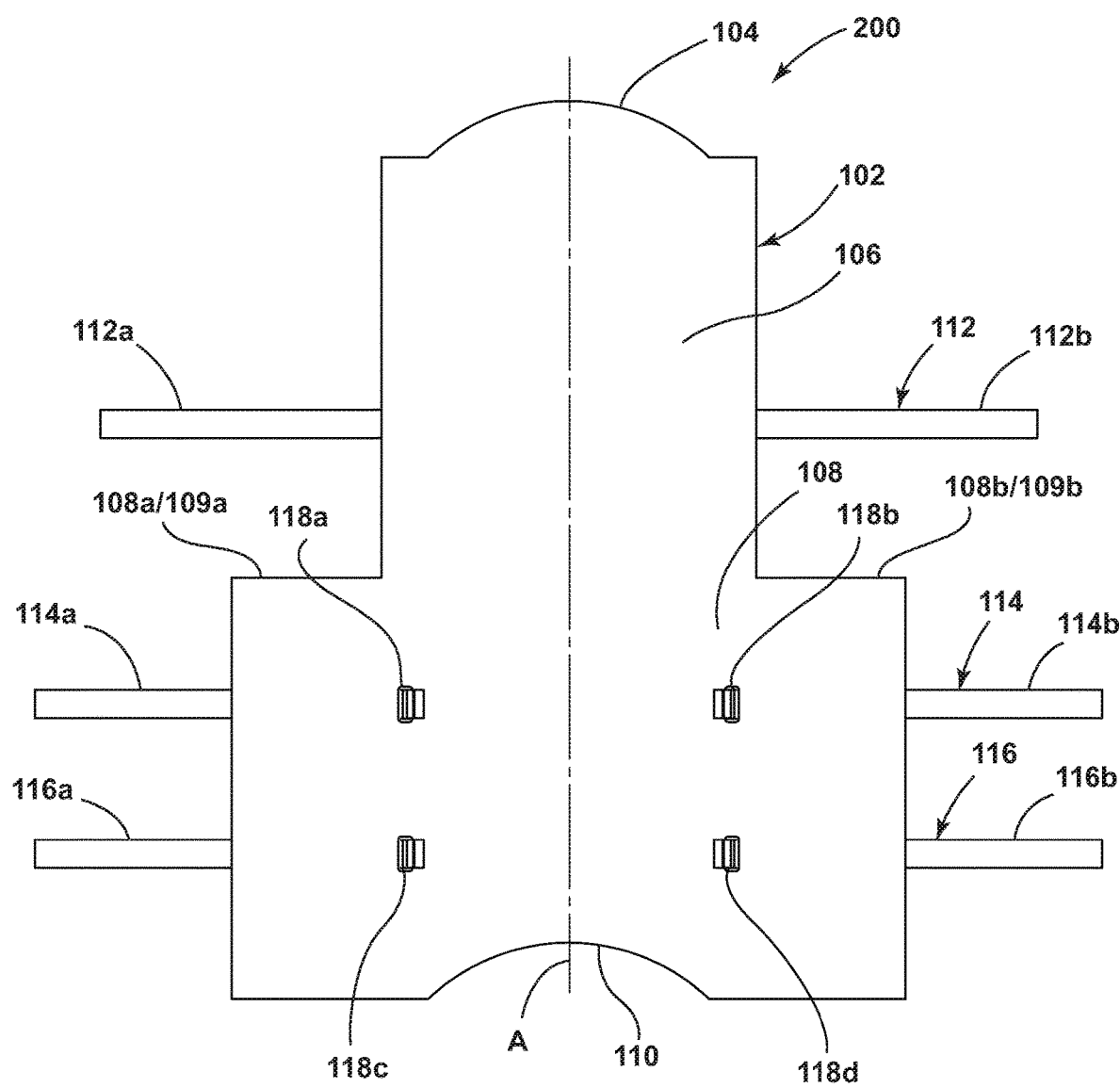
FIG. 16 illustrates a front view of an exemplary positioning system of the present disclosure.
Figure 17:
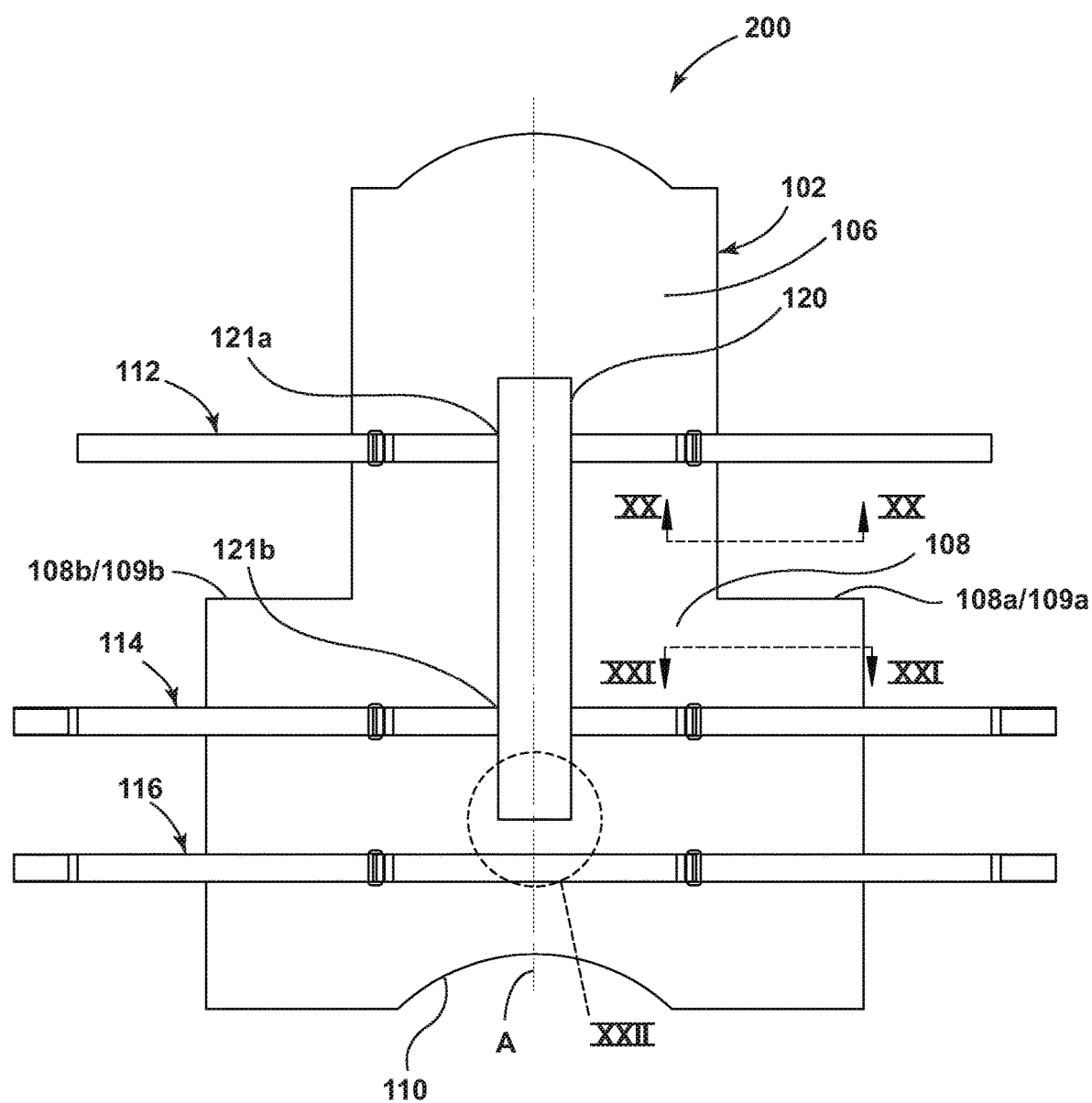
FIG. 17 illustrates a rear view of the exemplary positioning system of FIG. 16.
Figure 18:
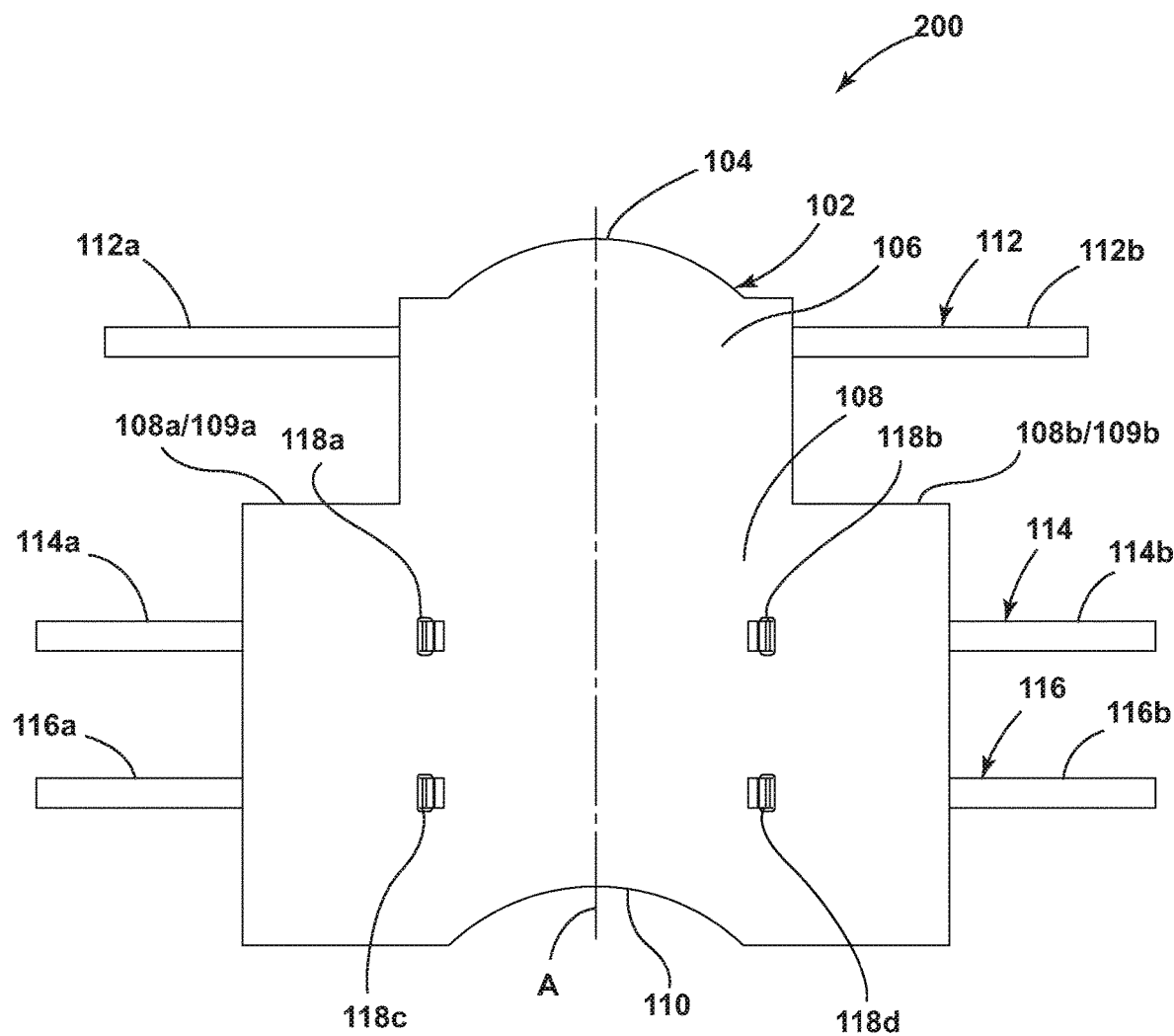
FIG. 18 illustrates a front view of another exemplary positioning system of the present disclosure.
Figure 19:
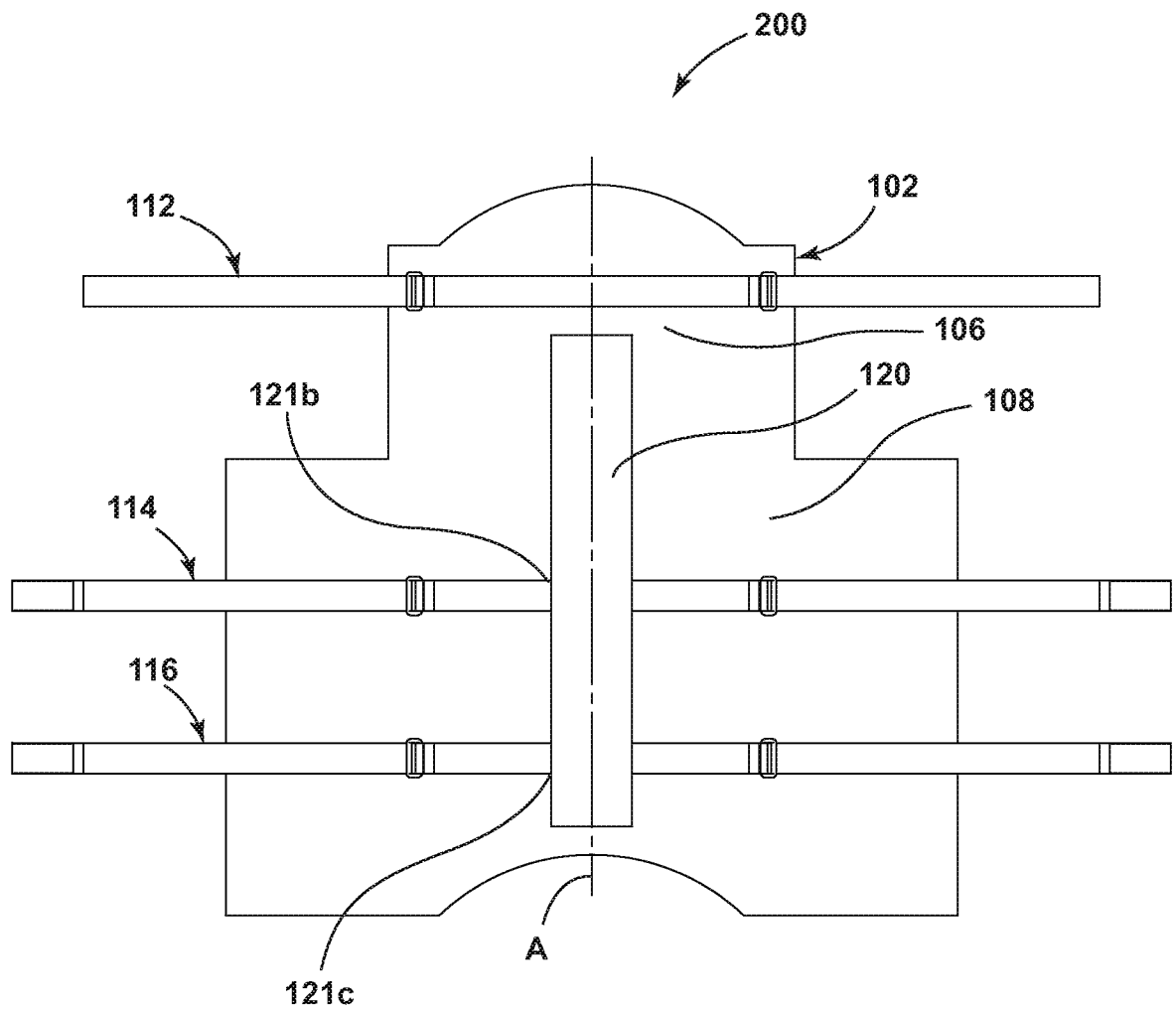
FIG. 19 illustrates a rear view of the exemplary positioning system of FIG. 18.

FIGS. 12-13 illustrate straps 114/116 secured to and through lower body portion 108 and between lower body portion 108 and arm support 109. Straps 112 may be similarly secured to and through upper body portion 106.

As shown in FIGS. 11 and 14-19, the pad body 102 may include an upper extension 104, an upper body or chest portion 106, a lower body or waist portion 108, and a bottom recess 110. The pad body 102 may include one or a plurality of slots or holes for receiving a first pad strap 112 along and/or through the upper body or chest portion, a second pad strap 114 along and/or through the lower body or waist portion 108, and a third pad strap 116 along and/or through the lower body or waist portion 108.

Figure 20:
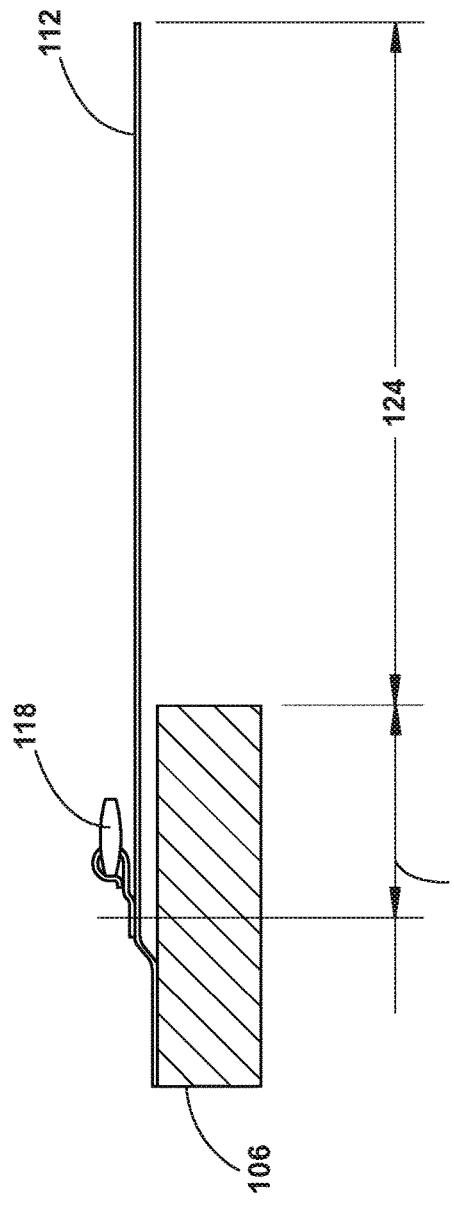
FIG. 20 illustrates a top view of an exemplary strap and buckle assembly of FIGS. 18-19.
Figure 21:
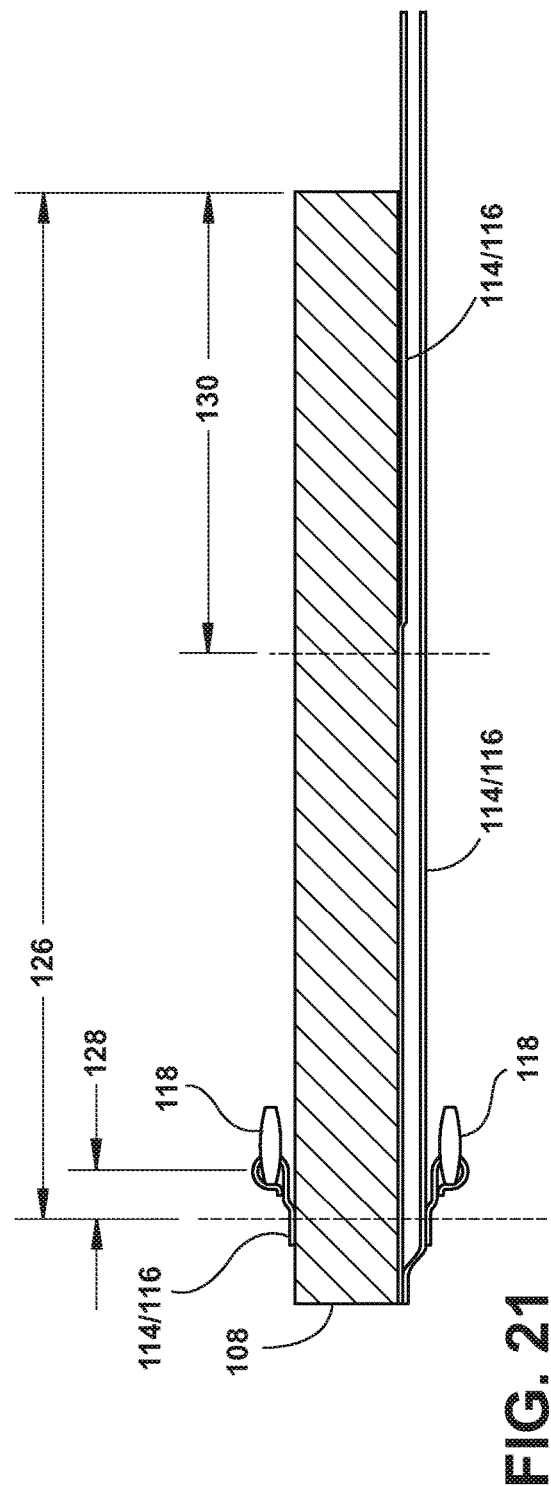
FIG. 21 illustrates a top view of an exemplary strap and buckle assembly of FIGS. 18-19.
Figure 22:
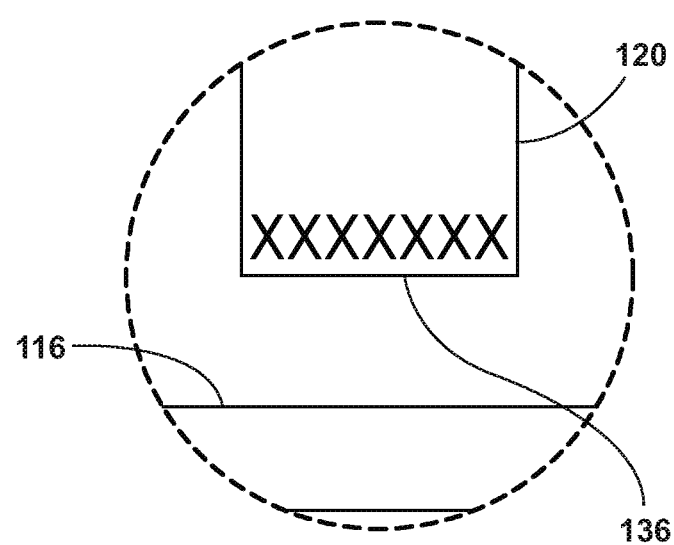
FIG. 22 illustrates a closer view of an exemplary strap assembly of the present disclosure.
Figure 23:
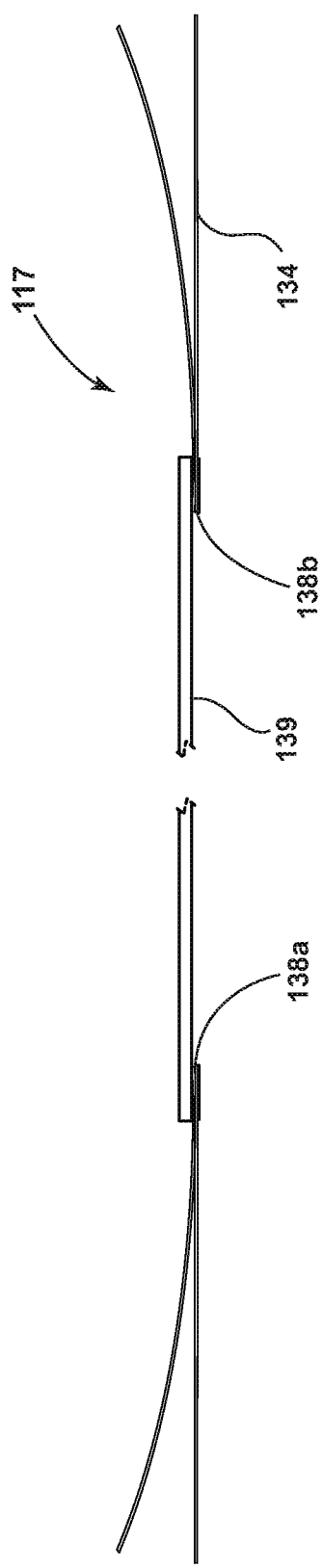
FIG. 23 illustrates a top view of a strap assembly of the present disclosure.
Figure 24:
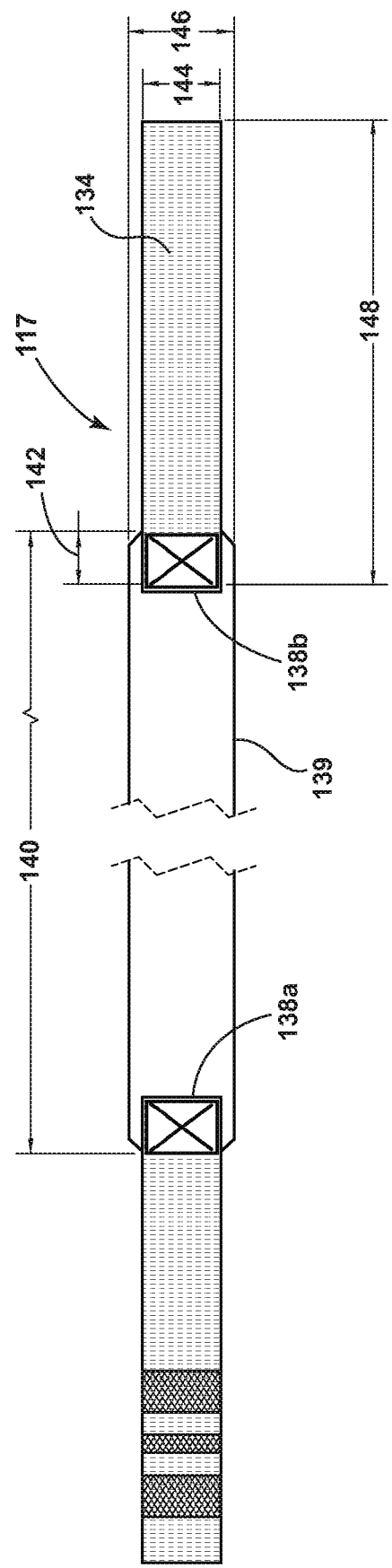
FIG. 24 illustrates a front view of the strap assembly of FIG. 24.

FIGS. 20-22 illustrate another arrangement of the components described above with respect to FIGS. 6-9, and FIGS. 23-24 illustrate another arrangement of the components described above with respect to FIG. 10. One or a plurality of body or chest straps 117 may be configured to engage the respective first, second, and third pad straps 112, 114, 116. The ends of the first, second, and third pad straps 112, 114, 116 may be configured as a hook to engage the respective one or a plurality of body or chest straps 117.

System 200 may include lower body portion 108 and arm portions or supports 109. Lower body portion 108 may include lower body extensions 108a, 108b. Arm extensions 109a, 109b may have a similar material and construction as lower body extensions 108a, 108b. The first and second arm extensions 109a, 109b may be positioned on respective sides of lower body portion 108 and configured to engage corresponding lower body extensions 108a, 108b. Arm extensions 109a, 109b may be in an corresponding arrangement to respective lower body extensions 108a, 108b so as to wrap or encompass the entire arm of the patient while allowing access to the shoulders and hands of the patient for injections, intravenous fluids and patient monitoring.

FIGS. 25-34 illustrate system 300 that may include all or any portions of systems 100 and/or 200 as described above with respect to FIGS. 1-24. As shown in FIGS. 25-34, system 300 may include similar or different structures and components than systems 100 and/or 200. System 300 may include a pad body 102. Pad body 102 may be made of a flexible material such as foam, e.g., medical grade foam.

Figure 25:
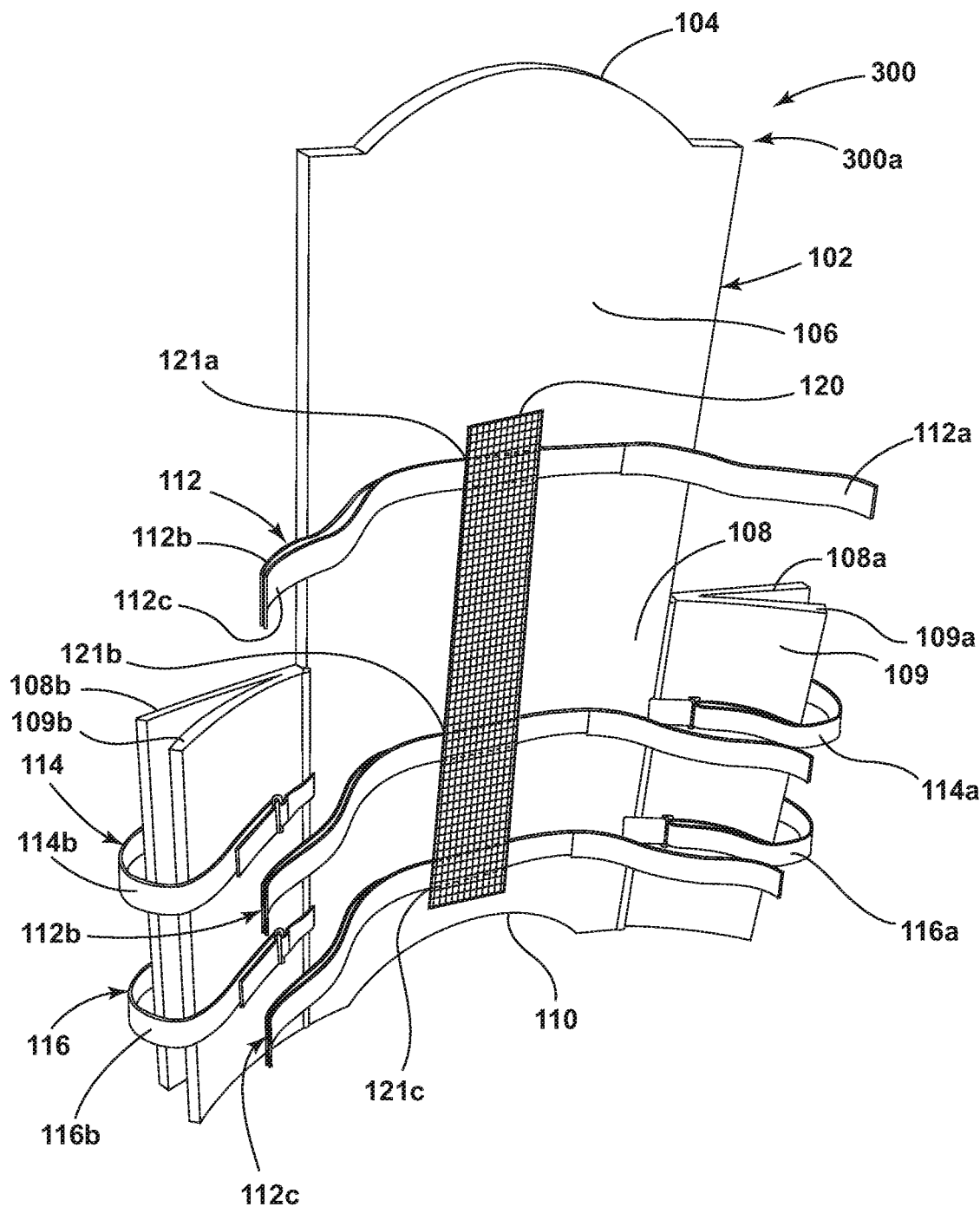
FIG. 25 illustrates an perspective view of another exemplary positioning system of the present disclosure.
Figure 26:
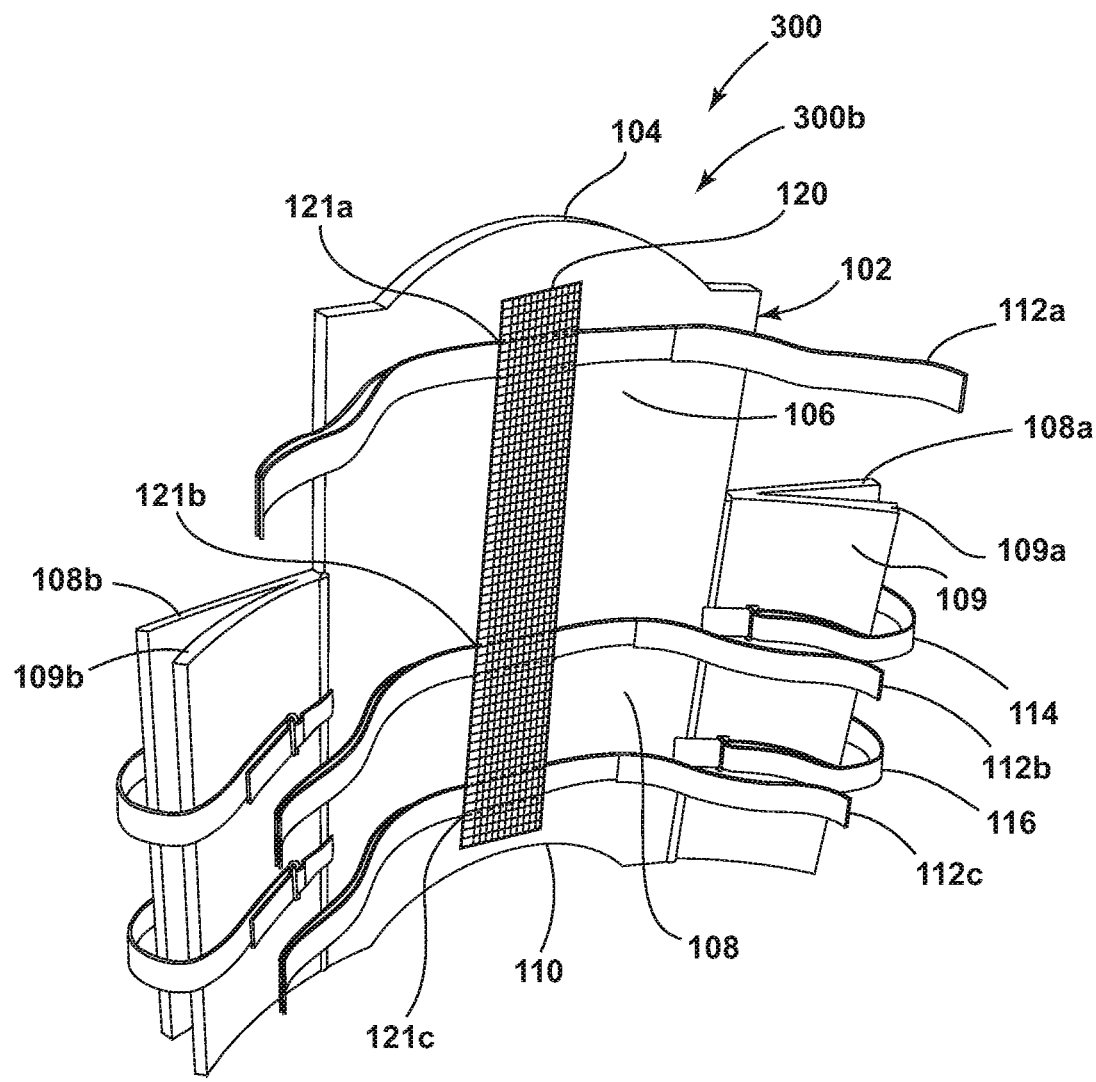
FIG. 26 illustrates an perspective view of another exemplary positioning system of the present disclosure.
Figure 27:
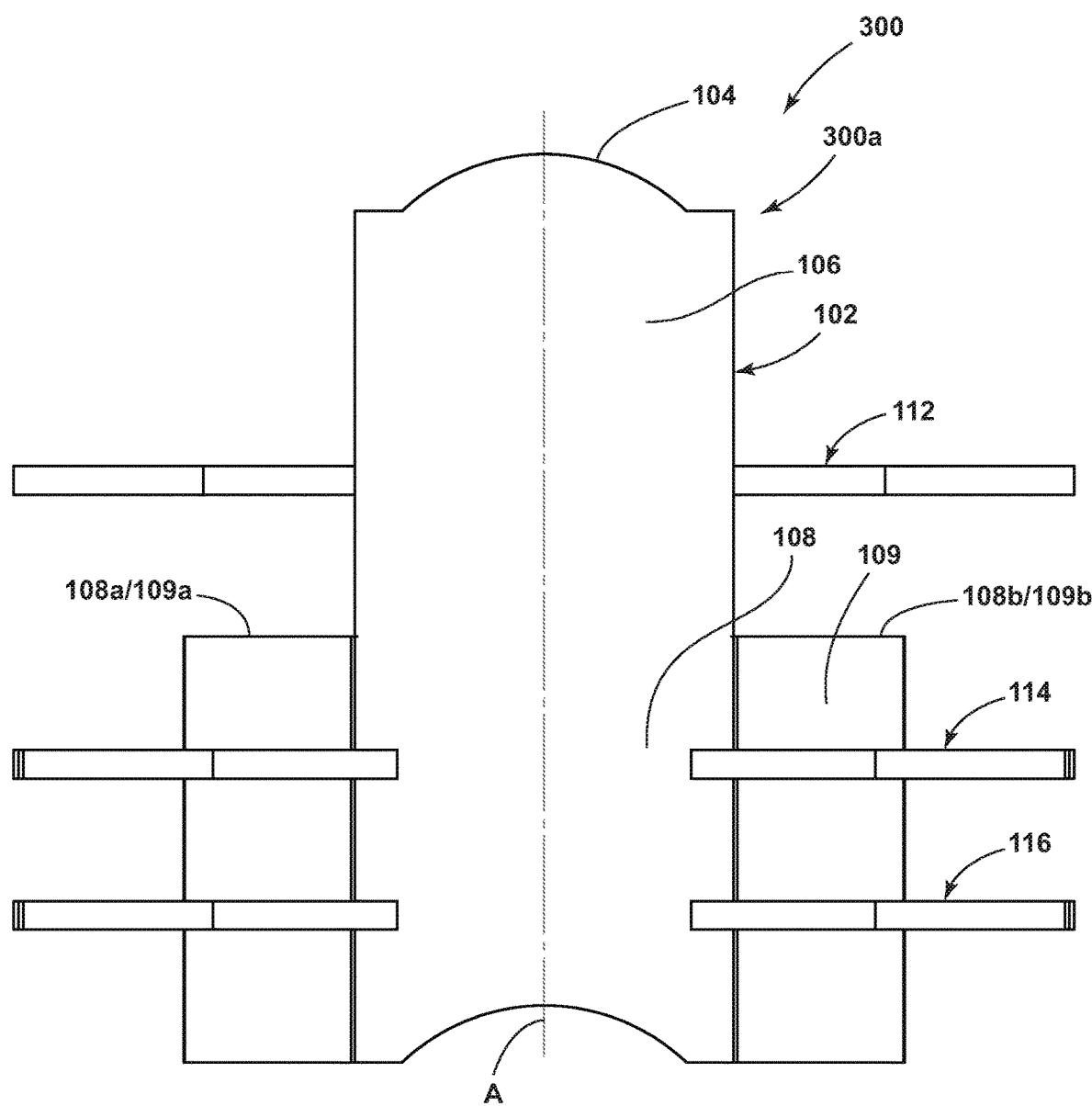
FIG. 27 illustrates a front view of the exemplary positioning system of FIG. 25.
Figure 28:
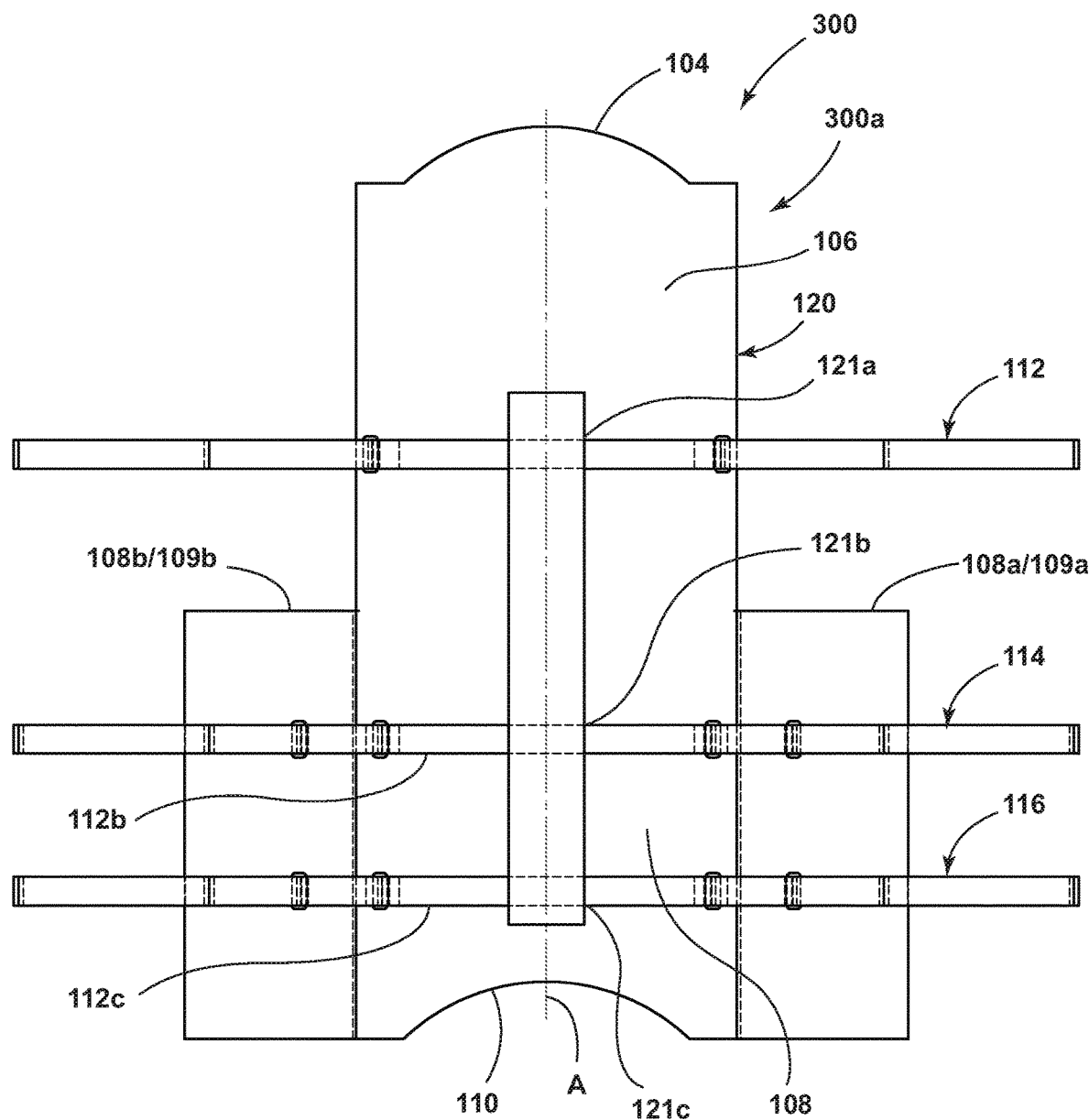
FIG. 28 illustrates a rear view of the exemplary positioning system of FIG. 25.
Figure 29:
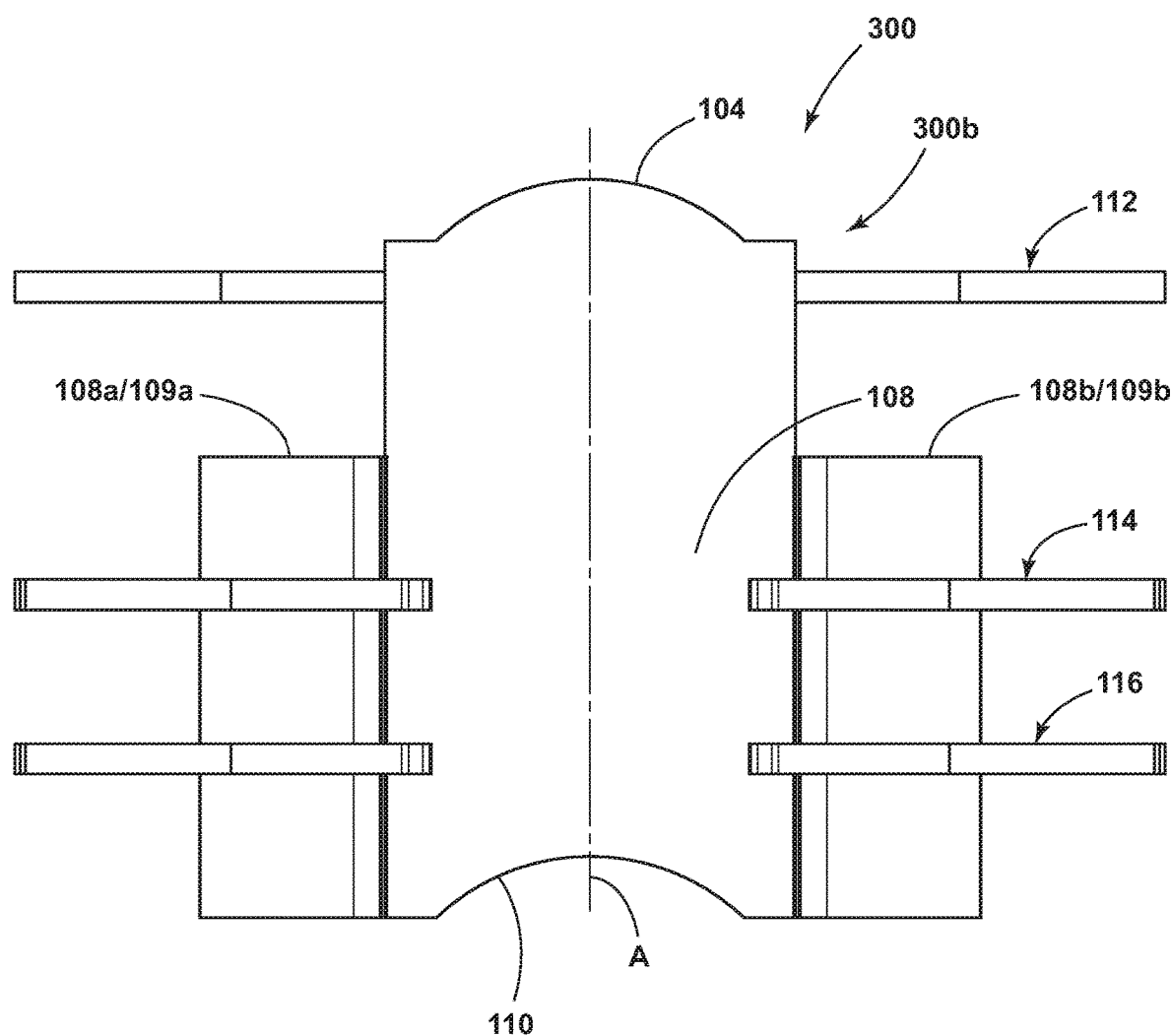
FIG. 29 illustrates a front view of the exemplary positioning system of FIG. 26.
Figure 30:
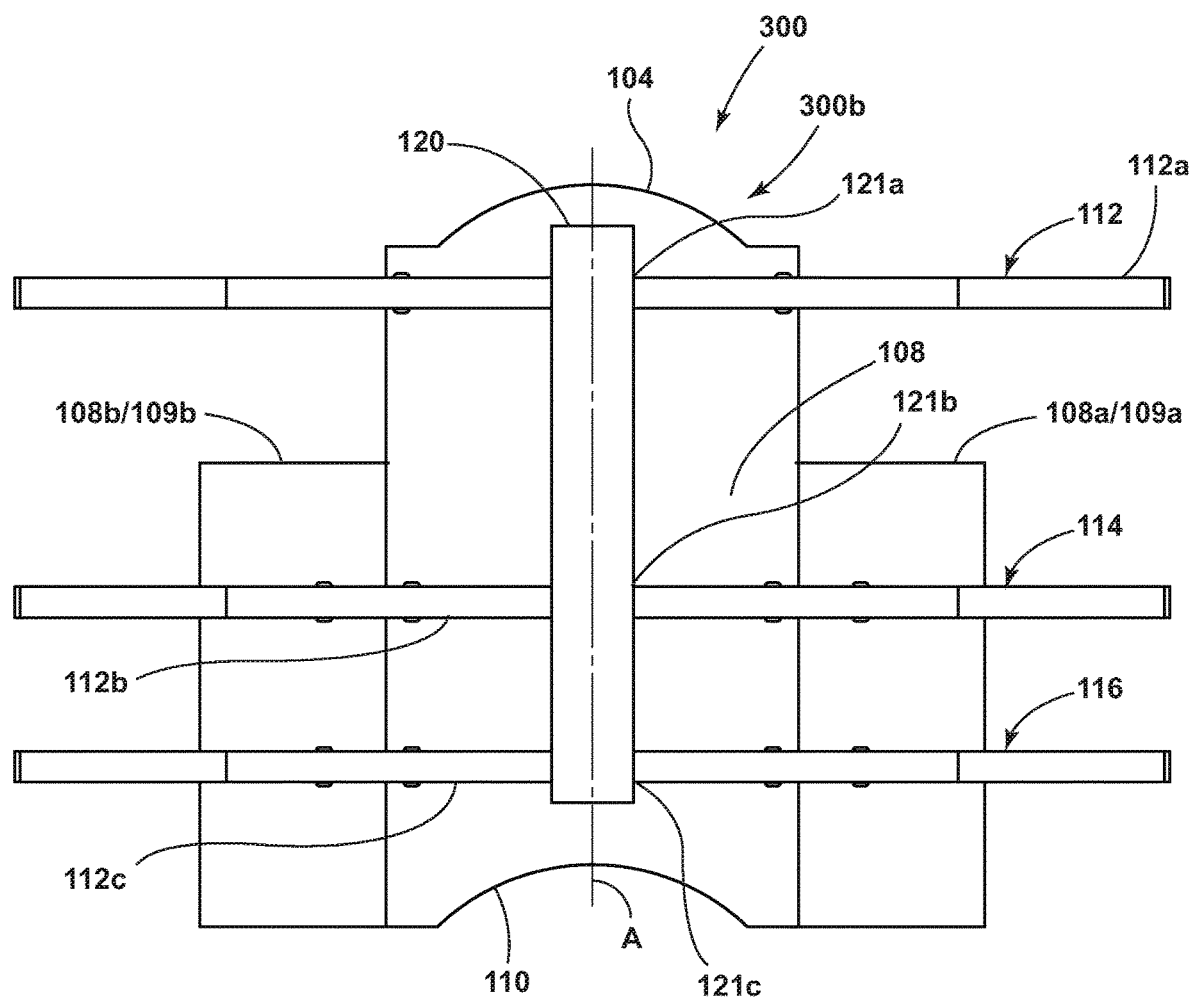
FIG. 30 illustrates a rear view of the exemplary positioning system of FIG. 26.

With further reference to FIGS. 25-30, system 300 may include the pad body 102 having an upper extension 104, an upper body or chest portion 106, a lower body or waist portion 108, arm portions 109, and a bottom recess 110. FIGS. 25 and 27-28 include system 300a having an elongated or longer length along longitudinal axis A and FIGS. 25 and 29-30 include system 300b having a compact or shorter length along longitudinal axis A.

Figure 31:
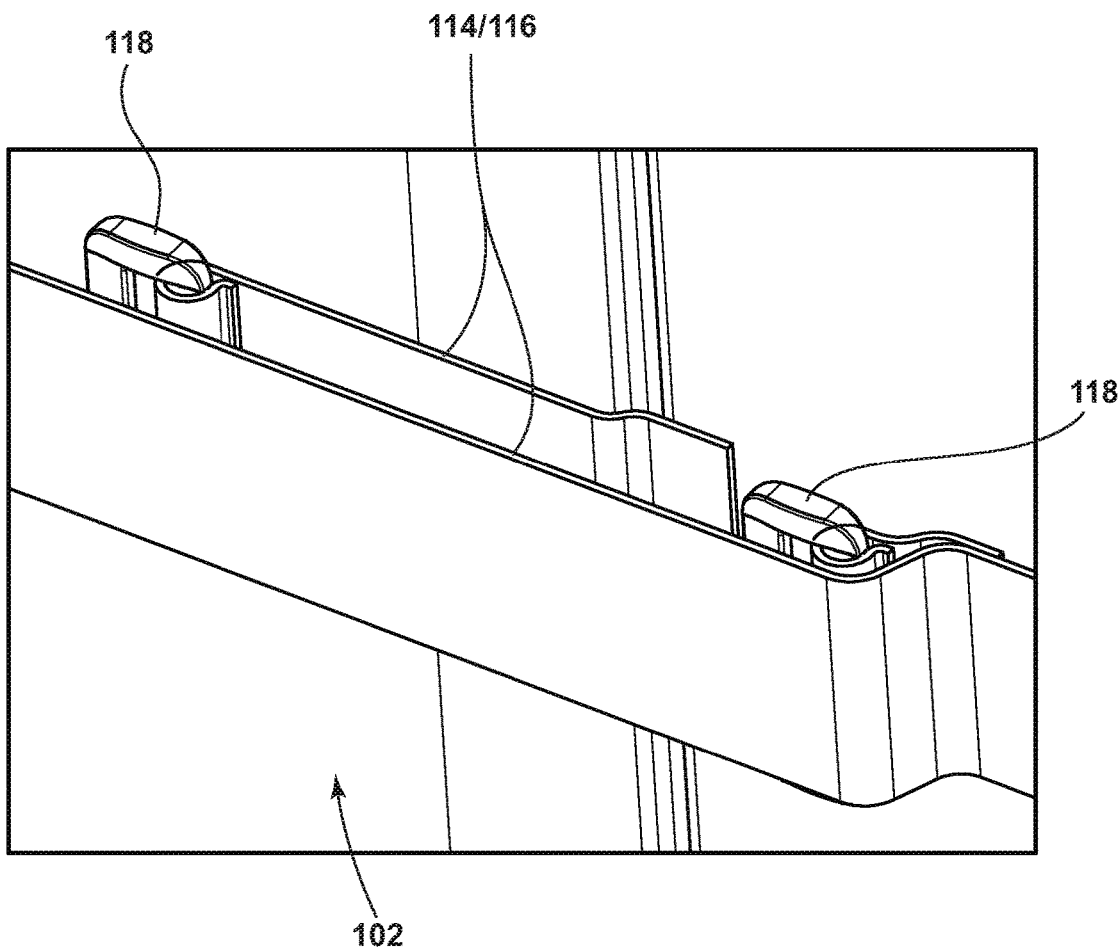
FIG. 31 illustrates a closer view of an exemplary positioning system including, for example, a strap and buckle assembly.
Figure 34:
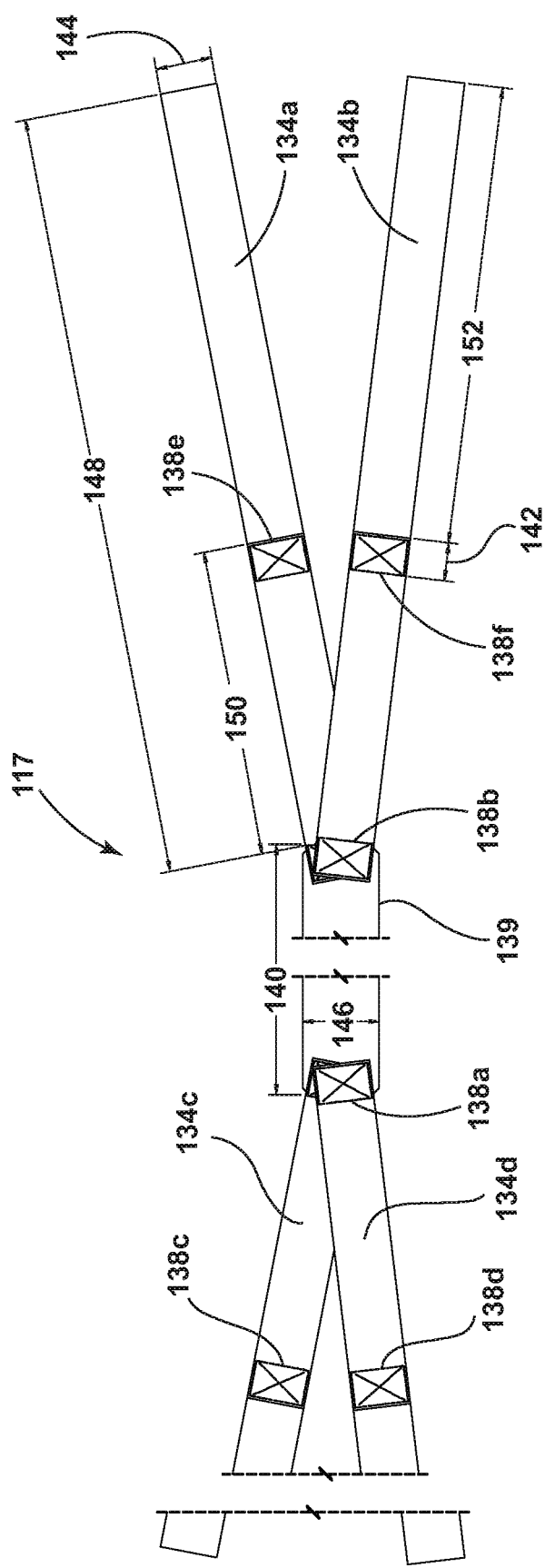
FIG. 34 illustrates a top view of a strap assembly of FIGS. 25-26.

System 300 may include pad straps 112a, 122b, 112c, 114, 116 as shown in FIGS. 25-33 and one or more body strap 117 as shown in FIG. 34 to engage any of pad straps 112a, 122b, 112c, 114, 116 and/or a surgical table. Referring to FIG. 31, buckles 118 may be positioned on respective pad straps 114/116. FIG. 32 includes a strap and buckle assembly having buckle 118 positioned on pad strap 112 that is secured to upper body portion 106. With reference to FIG. 33, buckles 118 may be positioned on respective portions of pad straps 114/116.

As shown in FIG. 34, strap 117 may include strap portions 134a-d, stitch patterns 138a-f on corresponding strap portions 134, and middle portion 139 having a first end with strap portions 138a, 138b at a first angle relative to each other and a second end with strap portions 138c, 138d at the first or a second angle relative to each other. Strap 117 may include a predefined dimension 140 (e.g., about 20 inches), a predefined dimension 142 (e.g., about 1 inch), a predefined dimension 144 (e.g., about 1.5 inches), a predefined dimension 146 (e.g., about 2 inches), a predefined dimension 148 (e.g., about 20 inches), and a predefined dimension 150 (e.g., about 8 inches), and a predefined dimension 152 (e.g., about 12 inches).

The pad body 102 may include one or a plurality of slots or holes for receiving one or a plurality of pad and/or body straps, e.g., a first pad strap 112 along and/or through the upper body or chest portion, a second pad strap 114 along and/or through the lower body or waist portion 108, and a third pad strap 116 along and/or through the lower body or waist portion 108. One or a plurality of body or chest straps 117 configured to engage the respective first, second, and third pad straps 112, 114, 116, side rails of a surgical table, or any combination thereof. The ends of the first, second, and third pad straps 112, 114, 116 may be configured as a hook to engage the respective one or a plurality of body or chest straps 117, side rails of the surgical table, or any combination thereof. The system 300 may include support strip 120.

Any of system 100, 200 and 300 may be configured as a positioning system for securing a patient relative to a surgical table. A system may include a pad body 102, an upper body portion 106 with an upper extension 104, a lower body portion 108 with first and second lower body extensions 108a, 108b, first and second arm extensions or supports 109a, 109b corresponding to the respective first and second lower body extensions 108a, 108b, and a bottom recess in the lower body portion 110. The system may include a first pad strap 112 configured to be positioned through the upper body portion 106, a second pad strap 114 configured to be positioned through an upper portion of the lower body portion 108, and a third pad strap 116 configured to be positioned through a lower portion of the lower body portion 108. The system may include a plurality of body straps 117 configured to engage at least one of the first, second, and third pad straps 112, 114, 116 and side rails of the surgical table. The first and second lower body extensions 108a, 108b may be configured to be positioned between a waist of a patient and respective first and second arms of the patient. The first arm extension 109a and first lower body extension 108a may be configured to wrap around the first arm of the patient, and the second arm extension 109b and second lower body extension 108b are configured to wrap around the second arm of the patient. The system may include a plurality of buckles 118 on corresponding pad straps 112, 114, 116 or body straps 117.

The system may include a support strip 120. The support strip 120 may be attached to the pad body 102. The support strip 120 may be positioned along a central, longitudinal axis A of the pad body. The support strip 120 may form channels or passages 121 relative to the pad body 102. Channels 121 may be configured to receive at least one of the first, second and third pad straps 112, 114, 116 between the pad body 102 and the support strip 120. The support strip 120 may be configured to support a substantial portion of a weight of a patient. The support strip 120 may include an anti-slip tape. The support strip may be attached along a central, longitudinal axis A of the pad body 102 and transverse to the first, second, and third pad straps 112, 114, 116. Any of the plurality of body straps 117 or pad straps 112, 114, 116 may include a fastening side with a hook and loop fastener configured to engage itself or another one of the plurality of body straps 117 or pad straps 112, 114, 116.

The system may be configured for engagement between the first and second arm extensions 109a, 109b and the first and second lower body extensions 108a, 108b. This engagement, alone or in conjunction with the straps and support strip 120, may be configured to support a substantial portion or majority of a weight of the patient to resist slippage relative to a surgical table while in at least one of a Trendelenburg, reverse Trendelenburg and lateral tilt position.

Methods of providing and using systems 100, 200 and 300 are contemplated. The method may include providing the system in a folded configuration having, e.g., with 106 folded over 108 about a transverse fold and 108 and 109 over 108 with longitudinal folds. The method may further include placing the system in the folded configuration on a surgical table, aligning bottom recess 110 with an edge of the table, centering the system on the table, and unfolding portions 114 and 116 on the table. The method may include engaging pad straps 112, 114, and/or 116 through the side rails of the table and engaging pad straps 112, 114, and/or 116 through one or more buckles 118 on a back or table facing side of the system. The method may include unfolding lower body portions 108a, 108b and arm extensions 109a, 109b, wrapping lower body portions 108a, 108b and arm extensions 109a, 109b around the arms of the patient and each other, and engaging pad straps 112, 114 and/or 116 around the respective lower body portions 108a, 108b and arm extensions 109a, 109b. The method may include positioning body straps 117 over the body and arms of the patient and engaging body straps 117 to the side rails of the table or pad straps 112, 114, 116. The method may include tilting the table to a prescribed angle for the medical procedure while the system restricts or prevents movement of the patient relative to the table. Methods may include a combination of any or all of these steps.

It will be appreciated that the aforementioned method and devices may be modified to have some components and steps removed, or may have additional components and steps added, all of which are deemed to be within the spirit of the present disclosure. None of the components or steps herein are essential elements nor is their interdependency required. Even though the present disclosure has been described in detail with reference to specific embodiments, it will be appreciated that the various modifications and changes can be made to these embodiments without departing from the scope of the present disclosure as set forth in the claims. The specification and the drawings are to be regarded as an illustrative thought instead of merely restrictive thought.

What is claimed is:

1. A positioning system comprising:
   a pad body having a longitudinal axis and first and second transverse ends on opposing sides of the longitudinal axis, the pad body including
   an upper body portion, and
   a lower body portion with first and second lower body extensions, and first and second arm extensions corresponding to the respective first and second lower body extensions,
   wherein the first and second arm extensions are respectively connected to the first and second lower body extensions such that the first arm extension and first lower body extension form a first common end that is connected to and extends in a first bifurcated configuration from the first transverse end of the pad body, the first common end sharing a common edge with the first lower body extension and the first transverse end of the pad body, and the second arm extension and second lower body extension form a second common end that is connected to and extends in a second bifurcated configuration from the second transverse end of the pad body, the second common end sharing a common edge with the second lower body extension and the second transverse end of the pad body;
   a plurality of pad straps configured to be positioned through at least one of the upper body and lower body portions; and
   a plurality of body straps configured to engage at least one of the plurality of pad straps.

2. The system of claim 1, further comprising a support strip attached to the pad body, wherein the support strip is positioned along the longitudinal axis of the pad body, the support strip forms channels configured to receive at least one of the plurality of pad straps between the pad body and the support strip, and the support strip is configured to support a portion of a weight of a patient.

3. The system of claim 2, wherein the support strip includes an anti-slip tape.

4. The system of claim 2, wherein the support strip is attached along the longitudinal axis of the pad body and transverse to the plurality of pad straps.

5. The system of claim 1, further comprising:
   first and second buckles on corresponding first and second portions of a first one of the plurality of pad straps; and
   third and fourth buckles on corresponding first and second portions of a second one of the plurality of pad straps.

6. The system of claim 1, wherein at least one of the plurality of body or pad straps includes a fastening side with a hook and loop fastener.

7. The system of claim 1, wherein engagement between the first and second arm extensions and the first and second lower body extensions is configured to support a portion of a weight of a patient to resist slippage relative to a surgical table while in at least one of a Trendelenburg, reverse Trendelenburg and lateral tilt position.

8. A method of a positioning system, comprising:
   providing a pad body having a longitudinal axis and first and second transverse ends on opposing sides of the longitudinal axis, the pad body including an upper body portion, a lower body portion with first and second lower body extensions, and first and second arm extensions opposing the respective first and second lower body extensions, wherein the first and second arm extensions are respectively connected to the first and second lower body extensions such that the first arm extension and first lower body extension form a first common end that is connected to and extends in a first bifurcated configuration from the first transverse end of the pad body, the first common end sharing a common edge with the first lower body extension and the first transverse end of the pad body, and the second arm extension and second lower body extension form a second common end that is connected to and extends in a second bifurcated configuration from the second transverse end of the pad body, the second common end sharing a common edge with the second lower body extension and the second transverse end of the pad body;
   providing a plurality of pad straps configured to be positioned through at least one of the upper body and lower body portions; and
   providing a plurality of body straps configured to engage at least one of the plurality of pad straps.

9. The method of claim 8, further comprising:
   attaching a support strip to the pad body, wherein the support strip is positioned along the longitudinal axis of the pad body;

forming channels by the support strip for receiving at least one of the plurality of pad straps between the pad body and the support strip; and supporting by the support strip a portion of a weight of a patient.

10. The method of claim 9, wherein the support strip includes an anti-slip tape.

11. The method of claim 9, further comprising:
attaching the support strip along the longitudinal axis of the pad body and transverse to the plurality of pad straps.

12. The method of claim 8, further comprising:
providing first and second buckles on corresponding first and second portions of a first one of the plurality of pad straps; and
providing third and fourth buckles on corresponding first and second portions of a second one of the plurality of pad straps.

13. The method of claim 8, further comprising:
engaging the first and second arm extensions and the respective first and second lower body extensions to support a portion of a weight of a patient to resist slippage relative to a surgical table while in at least one of a Trendelenburg, reverse Trendelenburg and lateral tilt position.

14. A positioning system comprising:
a pad body having a longitudinal axis and first and second transverse ends on opposing sides of the longitudinal axis, the pad body including
an upper body portion with an upper extension,
a lower body portion having first and second lower body extensions, and first and second arm extensions corresponding to the respective first and second lower body extensions, and
a bottom recess in the lower body portion;
a first pad strap configured to be positioned through the upper body portion;
a second pad strap configured to be positioned through the lower body portion;
a third pad strap configured to be positioned through the lower body portion;
a plurality of body straps configured to engage at least one of the first, second, and third pad straps; and
a support strip attached to the pad body and forming channels to receive at least one of the first, second and third pad straps between the pad body and the support strip,
wherein the first and second lower body extensions are configured to be positioned between a waist of a patient and respective first and second arms of the patient,
wherein the first and second arm extensions are respectively connected to the first and second lower body extensions such the first arm extension and first lower body extension are connected to and configured to extend from the first transverse end to wrap around the first arm of the patient, and the second arm extension and second lower body extension are connected to and configured to extend from the second transverse end to wrap around the second arm of the patient;
wherein the support strip is attached along the longitudinal axis of the pad body and transverse to the first, second, and third pad straps, and
wherein the first arm extension and the first lower body extension form a first common end that is connected to and extends in a first bifurcated configuration from the first transverse end of the pad body, the first common end sharing a common edge with the first lower body extension and the first transverse end of the pad body, and the second arm extension and second lower body extension form a second common end that is connected to and extends in a second bifurcated configuration from the second transverse end of the pad body, the second common end sharing a common edge with the second lower body extension and the second transverse end of the pad body.

15. The system of claim 14, wherein the support strip is positioned along the longitudinal axis of the pad body, and the support strip is configured to support a portion of a weight of the patient.

16. The system of claim 15, wherein the support strip includes an anti-slip tape.

17. The system of claim 14, further comprising:
a first buckle on a first portion of the second pad strap;
a second buckle on a second portion of the second pad strap;
a third buckle on a first portion of the third pad strap; and
a fourth buckle on a second portion of the third pad strap.

18. The system of claim 14, wherein at least one of the first, second and third pad straps or at least one of the plurality of body straps includes a fastening side with a hook and loop fastener.

19. The system of claim 14, wherein engagement between the first and second arm extensions and the first and second lower body extension is configured to support a portion of a weight of the patient to resist slippage relative to a surgical table while in at least one of a Trendelenburg, reverse Trendelenburg and lateral tilt position.

* * * * *